US010786039B2

(12) United States Patent
Kohatsu et al.

(10) Patent No.: US 10,786,039 B2
(45) Date of Patent: Sep. 29, 2020

(54) ARTICLE OF FOOTWEAR COMPRISING A SOLE MEMBER WITH APERTURES

(71) Applicant: NIKE, Inc., Beaverton, OR (US)

(72) Inventors: Shane S. Kohatsu, Portland, OR (US); Christopher S. Cook, Portland, OR (US); Bret Schoolmeester, Banks, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

(21) Appl. No.: 15/840,175

(22) Filed: Dec. 13, 2017

(65) Prior Publication Data
US 2018/0098602 A1   Apr. 12, 2018

Related U.S. Application Data

(62) Division of application No. 14/722,758, filed on May 27, 2015, now Pat. No. 9,861,159.

(51) Int. Cl.
| | |
|---|---|
| *A43B 13/18* | (2006.01) |
| *A43D 1/02* | (2006.01) |
| *A43B 13/14* | (2006.01) |
| *A43D 119/00* | (2006.01) |
| *A61B 5/103* | (2006.01) |

(52) U.S. Cl.
CPC ............ *A43B 13/186* (2013.01); *A43B 13/14* (2013.01); *A43B 13/141* (2013.01); *A43B 13/181* (2013.01); *A43D 1/02* (2013.01); *A43D 119/00* (2013.01); *A61B 5/1036* (2013.01)

(58) Field of Classification Search
CPC ... A43B 7/1405; A43B 7/1415; A43B 7/1485; A43B 13/181; A43B 13/186; A43B 13/188; A43B 17/02; A43B 7/14; A43B 7/18
USPC ....................................... 36/28, 29; 705/26.5
See application file for complete search history.

(56) References Cited

U.S. PATENT DOCUMENTS

| | | | |
|---|---|---|---|
| 1,785,410 A | 12/1930 | Gilkerson | |
| 2,150,057 A | 3/1939 | Fisch | |
| 2,885,797 A | 5/1959 | Chrencik | |
| 2,983,056 A * | 5/1961 | Murawski | A43B 13/12 36/29 |
| 3,253,355 A | 5/1966 | Menken | |
| 3,418,731 A | 12/1968 | Anciaux | |

(Continued)

FOREIGN PATENT DOCUMENTS

| | | |
|---|---|---|
| CA | 2107507 A1 | 4/1994 |
| DE | 4333597 A1 | 4/1994 |

(Continued)

OTHER PUBLICATIONS

Aug. 26, 2016 (WO) International Search Report and Written Opinion—App PCT/US2016/032006.

*Primary Examiner* — Heather Mangine
(74) *Attorney, Agent, or Firm* — Banner & Witcoff, Ltd.

(57) ABSTRACT

An article of footwear includes an upper and a sole structure with a sole member. The sole member can be manufactured using a cushioning sole system that provides different cushioning characteristics to a sole member using varying patterns of apertures. A user's foot morphology and/or preferences may be used to design the sole member. The sole member can include a set of apertures that are formed along various surfaces of the sole member.

20 Claims, 15 Drawing Sheets

(56) References Cited

U.S. PATENT DOCUMENTS

| | | | | |
|---|---|---|---|---|
| 3,785,646 A * | 1/1974 | Ruskin | A43B 3/0031 | 36/132 |
| 4,235,026 A | 11/1980 | Plagenhoef | | |
| 4,322,891 A * | 4/1982 | Inohara | A43B 13/206 | 36/29 |
| 4,364,189 A | 12/1982 | Bates | | |
| 4,445,284 A * | 5/1984 | Sakutori | A43B 7/081 | 36/28 |
| 4,494,322 A * | 1/1985 | Klagmann | A43B 13/186 | 36/28 |
| 4,506,461 A * | 3/1985 | Inohara | A43B 13/206 | 36/29 |
| 4,523,393 A * | 6/1985 | Inohara | A43B 13/206 | 36/29 |
| 4,624,061 A | 11/1986 | Wezel et al. | | |
| 4,798,009 A * | 1/1989 | Colonel | A43B 13/181 | 36/28 |
| 4,888,887 A * | 12/1989 | Solow | A43B 7/082 | 36/3 R |
| 4,894,932 A * | 1/1990 | Harada | A43B 7/088 | 36/29 |
| 4,956,927 A | 9/1990 | Misevich et al. | | |
| 5,025,573 A * | 6/1991 | Giese | A43B 13/12 | 36/28 |
| 5,044,096 A | 9/1991 | Polegato | | |
| 5,068,983 A | 12/1991 | Marc | | |
| 5,084,987 A * | 2/1992 | Flemming | A43B 1/0009 | 36/28 |
| 5,381,607 A * | 1/1995 | Sussmann | A43B 13/181 | 36/28 |
| 5,699,627 A * | 12/1997 | Castro | A43B 1/0045 | 36/28 |
| 5,799,413 A | 9/1998 | Argyris | | |
| 5,845,418 A * | 12/1998 | Chi | A43B 17/03 | 36/3 B |
| 6,160,264 A * | 12/2000 | Rebiere | A61B 5/1074 | 12/1 R |
| 6,675,502 B1 | 1/2004 | Chen | | |
| 6,874,252 B2 * | 4/2005 | Nakano | A43B 5/08 | 36/3 A |
| 6,880,266 B2 * | 4/2005 | Schoenborn | A43B 7/142 | 36/28 |
| 6,955,094 B1 * | 10/2005 | Tarler | A43B 5/00 | 73/841 |
| 7,032,328 B2 * | 4/2006 | Wilson | A43B 1/0009 | 36/11.5 |
| 7,434,338 B2 * | 10/2008 | Pfander | A43B 7/144 | 36/141 |
| 7,464,490 B2 | 12/2008 | Lebo | | |
| 7,475,497 B2 | 1/2009 | Hoffer et al. | | |
| 7,584,122 B2 * | 9/2009 | Kozinn | A41H 1/00 | 705/26.5 |
| 7,607,241 B2 | 10/2009 | McDonald et al. | | |
| 7,707,746 B2 * | 5/2010 | Dean | A43B 13/181 | 36/35 B |
| 7,941,938 B2 | 5/2011 | Yu et al. | | |
| 8,219,461 B2 * | 7/2012 | Langvin | A43B 5/001 | 36/134 |
| 8,479,414 B2 | 7/2013 | Baker et al. | | |
| 8,521,616 B2 * | 8/2013 | End | G06Q 30/06 | 705/26.63 |
| 8,584,379 B2 | 11/2013 | Baucom et al. | | |
| 8,713,819 B2 | 5/2014 | Auger et al. | | |
| 8,752,307 B2 | 6/2014 | Cooper et al. | | |
| 9,460,557 B1 * | 10/2016 | Tran | B29C 64/386 | |
| 9,775,405 B2 * | 10/2017 | Kohatsu | A43B 13/186 | |
| 9,778,027 B1 * | 10/2017 | Smith | G01B 11/24 | |
| 9,867,425 B2 * | 1/2018 | Cook | A43B 13/12 | |
| 9,996,981 B1 * | 6/2018 | Tran | G06T 19/006 | |
| 2002/0158358 A1 * | 10/2002 | Franzene | A43D 1/025 | 264/40.1 |
| 2003/0217485 A1 | 11/2003 | Oishi et al. | | |
| 2004/0016148 A1 | 1/2004 | Chen | | |
| 2004/0024645 A1 | 2/2004 | Potter et al. | | |
| 2004/0143452 A1 * | 7/2004 | Pattillo | A43D 1/02 | 600/300 |
| 2004/0159015 A1 | 8/2004 | Dennis et al. | | |
| 2004/0168354 A1 | 9/2004 | Nguyen | | |
| 2004/0187350 A1 * | 9/2004 | Lacorazza | A43B 5/00 | 36/30 R |
| 2005/0061332 A1 * | 3/2005 | Greenawalt | A43D 1/025 | 128/882 |
| 2005/0071242 A1 | 3/2005 | Allen et al. | | |
| 2005/0171456 A1 * | 8/2005 | Hirschman | A61B 5/1036 | 600/592 |
| 2006/0156579 A1 | 7/2006 | Hoffer et al. | | |
| 2007/0043582 A1 * | 2/2007 | Peveto | A43B 3/26 | 705/1.1 |
| 2007/0043630 A1 * | 2/2007 | Lyden | A43B 1/0081 | 705/26.41 |
| 2007/0163147 A1 * | 7/2007 | Cavanagh | A43B 17/00 | 36/44 |
| 2008/0292179 A1 * | 11/2008 | Busch | A43B 17/00 | 382/154 |
| 2010/0126041 A1 | 5/2010 | Francis | | |
| 2011/0061263 A1 | 3/2011 | Everz-Vaz | | |
| 2011/0099850 A1 * | 5/2011 | Van Dyck | A43B 3/0031 | 36/136 |
| 2011/0162234 A1 | 7/2011 | Dean | | |
| 2012/0089477 A1 * | 4/2012 | Dean | A43B 3/24 | 705/26.5 |
| 2012/0180335 A1 * | 7/2012 | Mahoney | A43B 7/144 | 36/28 |
| 2012/0180336 A1 * | 7/2012 | Sullivan | A43B 7/144 | 36/31 |
| 2012/0198949 A1 * | 8/2012 | Xia | A43D 1/022 | 73/865.8 |
| 2013/0160223 A1 | 6/2013 | Bier et al. | | |
| 2013/0173413 A1 * | 7/2013 | Page | G06Q 30/00 | 705/26.5 |
| 2013/0173414 A1 * | 7/2013 | Page | G06O 30/0621 | 705/26.5 |
| 2013/0191240 A1 * | 7/2013 | Lasry | A43D 1/02 | 705/26.5 |
| 2013/0219746 A1 | 8/2013 | Chiu | | |
| 2013/0258085 A1 * | 10/2013 | Leedy | A43D 1/025 | 348/77 |
| 2014/0039657 A1 * | 2/2014 | Spector | A43B 17/00 | 700/97 |
| 2014/0182049 A1 | 7/2014 | Prust et al. | | |
| 2014/0182170 A1 * | 7/2014 | Wawrousek | A43B 7/14 | 36/103 |
| 2014/0223777 A1 * | 8/2014 | Whiteman | A43B 13/125 | 36/102 |
| 2014/0290094 A1 | 10/2014 | Miner | | |
| 2014/0366399 A1 | 12/2014 | Wakeland et al. | | |
| 2015/0165690 A1 * | 6/2015 | Tow | B33Y 80/00 | 700/119 |
| 2016/0066648 A1 * | 3/2016 | Lazarchik | A43B 3/108 | 36/30 R |
| 2016/0128433 A1 * | 5/2016 | Downing | A43B 3/0078 | 264/400 |
| 2016/0242502 A1 * | 8/2016 | Spanks | A43B 13/20 | |
| 2016/0345664 A1 * | 12/2016 | Kohatsu | A43B 13/186 | |
| 2016/0345666 A1 * | 12/2016 | Kohatsu | A43B 13/186 | |
| 2016/0345667 A1 * | 12/2016 | Kohatsu | A43B 13/186 | |
| 2016/0360828 A1 * | 12/2016 | Guyan | A43B 13/186 | |
| 2017/0245588 A1 * | 8/2017 | Cook | A43B 13/026 | |
| 2017/0245589 A1 * | 8/2017 | Cook | A43B 13/12 | |
| 2017/0332725 A1 * | 11/2017 | Hendrix | A43B 3/128 | |

FOREIGN PATENT DOCUMENTS

| | | |
|---|---|---|
| EP | 0074568 A1 | 3/1983 |
| EP | 0375306 A2 | 6/1990 |
| EP | 1795083 A1 | 6/2007 |
| GB | 1512745 A | 6/1978 |
| WO | 2014100462 A1 | 6/2014 |

\* cited by examiner

ARTICLE OF FOOTWEAR COMPRISING A SOLE MEMBER WITH APERTURES

RELATED APPLICATION DATA

This application is a divisional application based on co-pending U.S. patent application Ser. No. 14/722,758 titled "Article of Footwear Comprising a Sole Member with Apertures," filed May 27, 2015. U.S. patent application Ser. No. 14/722,758 is entirely incorporated herein by reference.

BACKGROUND

The present embodiments relate generally to articles of footwear, and in particular to articles with cushioning provisions and methods of making such articles.

Articles of footwear generally include two primary elements: an upper and a sole member. The upper is often formed from a plurality of material elements (e.g., textiles, polymer sheet layers, foam layers, leather, synthetic leather) that are stitched or adhesively bonded together to form a void on the interior of the footwear for comfortably and securely receiving a foot. More particularly, the upper forms a structure that extends over the instep and toe areas of the foot, along medial and lateral sides of the foot, and around a heel area of the foot. The upper may also incorporate a lacing system to adjust the fit of the footwear, as well as permitting entry and removal of the foot from the void within the upper. In addition, the upper may include a tongue that extends under the lacing system to enhance adjustability and comfort of the footwear, and the upper may incorporate a heel counter.

The sole member is secured to a lower portion of the upper so as to be positioned between the foot and the ground. In athletic footwear, for example, the sole member includes a midsole and an outsole. The various sole components may be formed from a polymer foam material that attenuates ground reaction forces (i.e., provides cushioning) during walking, running, and other ambulatory activities. The sole may also include fluid-filled chambers, plates, moderators, or other elements that further attenuate forces, enhance stability, or influence the motions of the foot, for example.

SUMMARY

In one aspect, the present disclosure is directed to a sole member for an article of footwear, comprising a sole member, the sole member including an outer surface, and the outer surface comprising an upper surface, a lower surface, and a sidewall. The sole member has an interior portion, where the interior portion is disposed between the upper surface, the lower surface, and the sidewall. Furthermore, the sole member has a set of apertures, where each aperture of the set of apertures is a blind-hole aperture. The set of apertures is disposed along a portion of the outer surface of the sole member, and each aperture of the set of apertures has a length extending through a portion of the interior portion of the sole member and opens to the outer surface. In addition, the set of apertures includes a first aperture, a second aperture disposed adjacent to the first aperture, and a third aperture disposed adjacent to the second aperture, where the length of the first aperture is less than the length of the second aperture, and where the length of the second aperture is less than the length of the third aperture. The set of apertures also includes a fourth aperture disposed adjacent to the third aperture, a fifth aperture disposed adjacent to the fourth aperture, and a sixth aperture disposed adjacent to the fifth aperture, where the length of the fourth aperture is greater than the length of the fifth aperture, and where the length of the fifth aperture is greater than the length of the sixth aperture.

In another aspect, the present disclosure is directed to a customized cushioning sole system for an article of footwear, where the system comprises a sole member, and the sole member includes an outer surface, where the outer surface comprises an upper surface, a lower surface, and a sidewall. The sole member has a set of apertures, where each of the apertures includes an opening disposed within the outer surface, where the openings associated with the set of apertures comprise a pattern, and where the pattern extends along at least one of the upper surface, the lower surface, and the sidewall of the sole member. Furthermore, each aperture of the set of apertures is a blind-hole aperture, and each aperture of the set of apertures has a length. The lengths of each of the apertures of the set of apertures vary according to a gradual progression.

In another aspect, the present disclosure is directed to a method for making a customized sole member for an article of footwear, the method comprising obtaining information related to a wearer's foot and producing a pattern of apertures. The method further comprises generating instructions to form the apertures in a sole member and executing the instructions to produce the customized sole member.

Other systems, methods, features and advantages of the embodiments will be, or will become, apparent to one of ordinary skill in the art upon examination of the following figures and detailed description. It is intended that all such additional systems, methods, features and advantages be included within this description and this summary, be within the scope of the embodiments, and be protected by the following claims.

BRIEF DESCRIPTION OF THE DRAWINGS

The embodiments can be better understood with reference to the following drawings and description. The components in the figures are not necessarily to scale, emphasis instead being placed upon illustrating the principles of the embodiments. Moreover, in the figures, like reference numerals designate corresponding parts throughout the different views.

DETAILED DESCRIPTION

FIGS. 1-5 depict different embodiments of a portion of a cushioning element. A cushioning element can include provisions for increasing flexibility, fit, comfort, and/or stability during deformation or use of the cushioning element or article incorporating the cushioning element. Some of the embodiments of cushioning elements as disclosed herein may be utilized in various articles of apparel. In one embodiment, the cushioning elements may be used in an article of footwear. For example, as discussed in further detail below, in one embodiment, portions of a sole structure or sole member may incorporate or otherwise include a cushioning element.

For consistency and convenience, directional adjectives are also employed throughout this detailed description corresponding to the illustrated embodiments. The term "lateral" or "lateral direction" as used throughout this detailed description and in the claims refers to a direction extending along a width of a component or element. For example, a lateral direction may be oriented along a lateral axis 190 of a foot (see FIG. 15), which axis may extend between a medial side and a lateral side of the foot. Additionally, the term "longitudinal" or "longitudinal direction" as used throughout this detailed description and in the claims refers to a direction extending across a length of an element or component (such as a sole member). In some embodiments, a longitudinal direction may be oriented along longitudinal axis 180, which axis may extend from a forefoot region to a heel region of a foot (see FIG. 5). It will be understood that each of these directional adjectives may also be applied to individual components of an article of footwear, such as an upper and/or a sole member. In addition, a vertical axis 170 refers to the axis perpendicular to a horizontal surface defined by longitudinal axis 180 and lateral axis 190.

Figure 1:
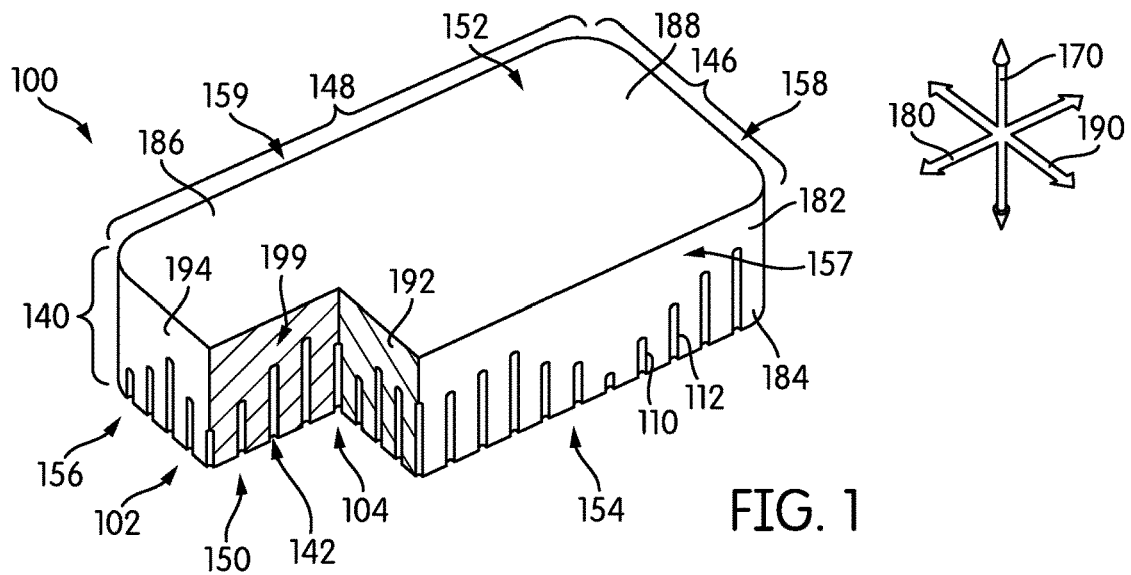
FIG. 1 is an isometric view of an embodiment of a cushioning element including apertures.
Figure 2:
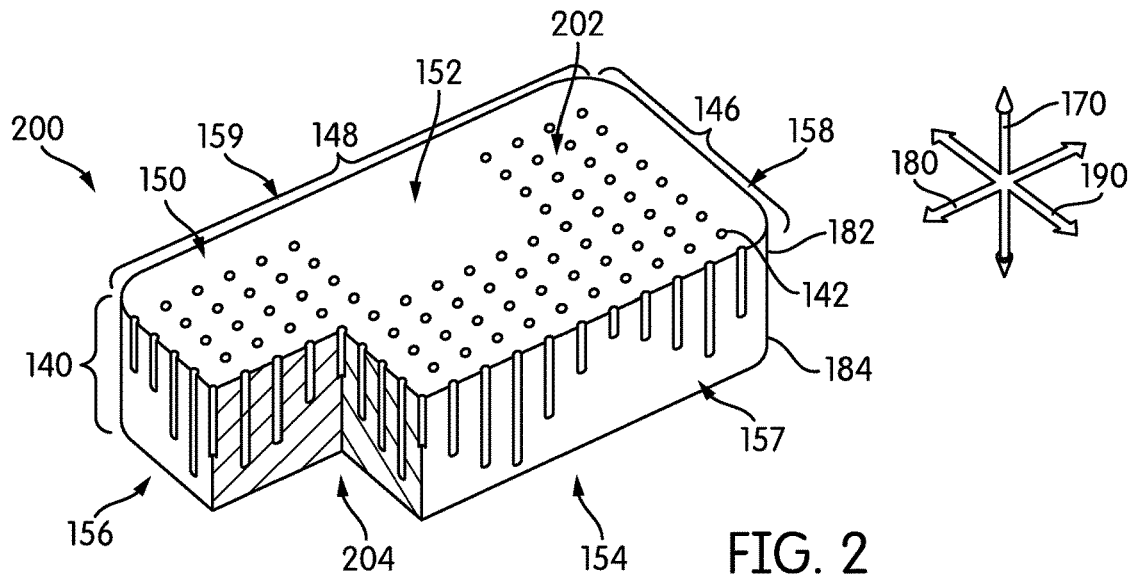
FIG. 2 is an isometric view of an embodiment of a cushioning element including apertures.
Figure 3:
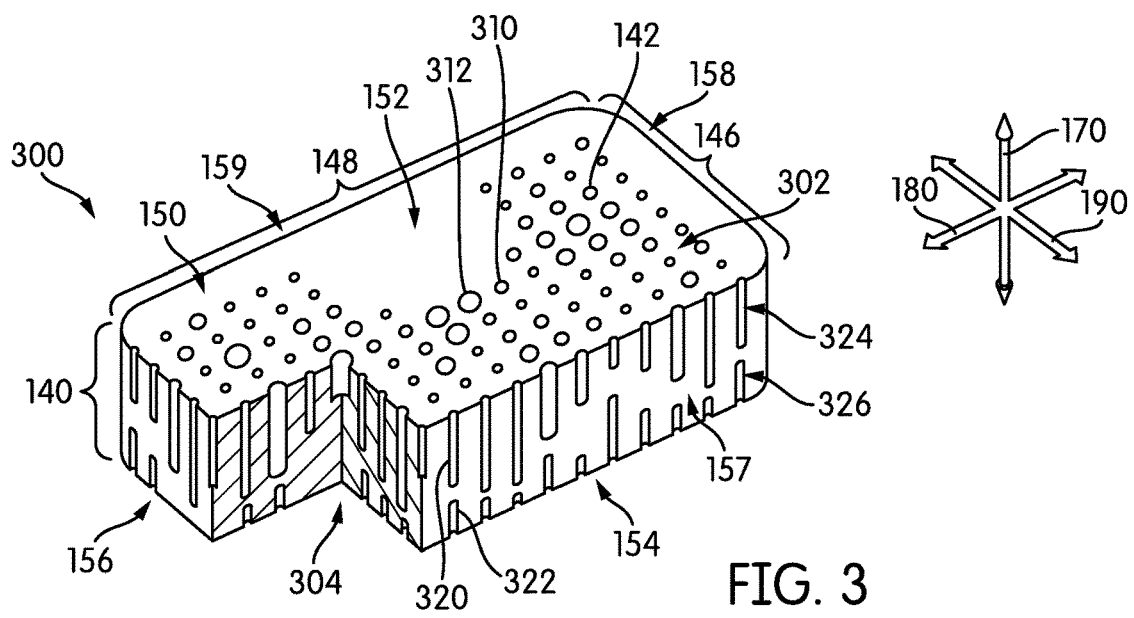
FIG. 3 is an isometric view of an embodiment of a cushioning element including apertures.
Figure 4:
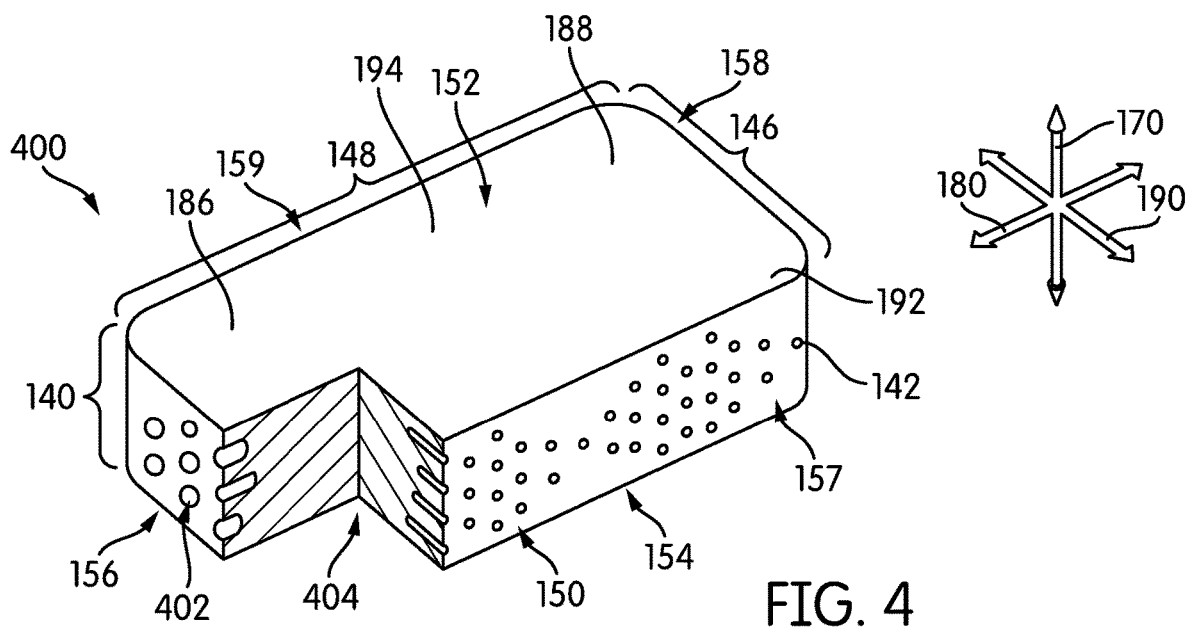
FIG. 4 is an isometric view of an embodiment of a cushioning element including apertures.
Figure 5:
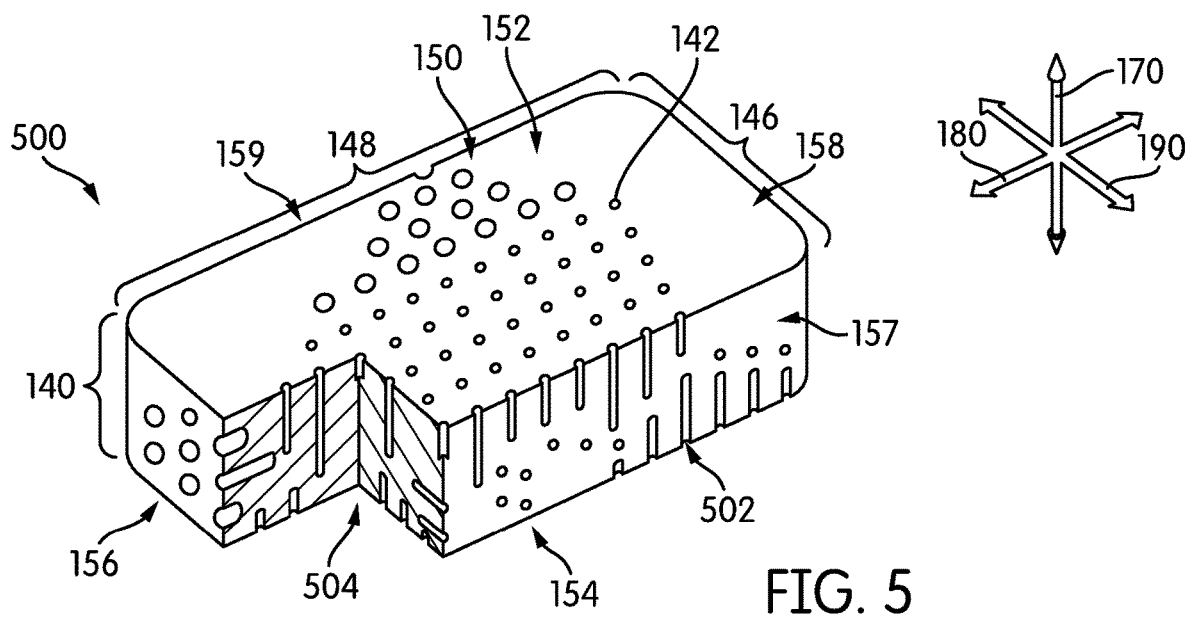
FIG. 5 is an isometric view of an embodiment of a cushioning element including apertures.

FIG. 1 depicts an embodiment of a first cushioning element ("first element") 100, FIG. 2 depicts an embodiment of a second cushioning element ("second element") 200, FIG. 3 depicts an embodiment of a third cushioning element ("third element") 300, FIG. 4 depicts an embodiment of a fourth cushioning element ("fourth element") 400, and FIG. 5 depicts an embodiment of a fifth cushioning element ("fifth element") 500. As shown in FIGS. 1-5, in some embodiments, a cushioning element can include one or more apertures 150. For purposes of this description, apertures 150 are openings, apertures, holes, tunnels, or spaces that are disposed within the cushioning element. Apertures 150 can include a void in some embodiments. Generally, apertures 150 are initially formed along an exterior or outer surface of the cushioning element, and can extend any distance, and along any orientation, through an interior portion 199 (e.g., the thickness, breadth, or width) of the cushioning element. It should be understood that the terms exterior or outer surface with reference to a sole member do not necessarily indicate whether the sole member is actually exposed to the outer elements. Instead, outer surface or exterior surface refers to the outermost, outward-facing layer of the sole member. Interior portion 199 can be disposed between an upper surface 152, a lower surface 154, and a sidewall in some embodiments. Throughout the specification, it should be understood that characteristics being described as associated with a single aperture or aperture set can also characterize any other aperture or aperture set that may be referred to in the various embodiments.

The embodiments described herein may also include or refer to techniques, concepts, features, elements, methods, and/or components from: (a) U.S. patent application Ser. No. 14/722,826, filed May 27, 2015, titled "Article of Footwear Comprising a Sole Member with Geometric Patterns," (b) U.S. patent application Ser. No. 14/722,740, filed May 27, 2015, titled "Article of Footwear Comprising a Sole Member with Regional Patterns," and (c) U.S. patent application Ser. No. 14/722,782, filed May 27, 2015, titled "Article of Footwear Comprising a Sole Member with Aperture Patterns," the entirety of each application being herein incorporated by reference.

In different embodiments, cushioning elements may comprise any three-dimensional shape or geometry, including regular or irregular shapes. For example, cushioning elements may be substantially flat or narrow, and/or relatively thick or wide. The geometry and dimensions of a cushioning element can be configured for the application or exercise in which it will be used. For illustrative purposes, in FIGS. 1-5, the portions of cushioning elements have a generally oblong rectangular three-dimensional shape. Furthermore, for purposes of reference, as shown in FIGS. 1-5, each cushioning element may include upper surface 152 and lower surface 154 that is disposed opposite of upper surface 152. In some cases, upper surface 152 can be disposed adjacent to or joined to another component, such as an upper (see FIGS. 25 and 26). In addition, in some cases, lower surface 154 can be a ground-contacting surface. However, in other cases, lower surface 154 may be disposed adjacent to another material (such as an outsole). The cushioning elements can further include additional exterior-facing surfaces. For example, as shown in FIGS. 1-5, the cushioning elements have four sidewalls, including a first side 156, a second side 157, a third side 158, and a fourth side 159. First side 156, second side 157, third side 158, and fourth side 159 may extend between upper surface 152 and lower surface 154. In addition, cushioning elements include a thickness 140 extending between upper surface 152 and lower surface 154 along vertical axis 170, and a width 146 extending from second side 157 to fourth side 159 along lateral axis 190, as well as a length 148 extending along longitudinal axis 180 from first side 156 to third side 158. As noted in FIG. 1, thickness 140 may include an upper portion 182 and a lower portion 184. Width 146 may include a forward portion 192 and a rear portion 194. Furthermore, length 148 may include a first side portion 186 and a second side portion 188. Upper surface 152, lower surface 154, and sidewalls as depicted herein are associated with an outer surface of the cushioning elements.

It should be understood that other embodiments can have a fewer or greater number of exterior surfaces, and that the cushioning elements and the different regions of cushioning elements shown herein are for illustrative purposes only. In other embodiments, cushioning elements may include any contour, and may be any size, shape, thickness, or dimension, including regular and irregular shapes.

In some embodiments, apertures 150 have a rounded shape. In other embodiments, apertures 150 may include a wide variety of other geometries, including regular and irregular shapes. Apertures 150 may have a cross-sectional shape that is round, square, or triangular, for example. In some embodiments, apertures 150 may have a variety of geometric shapes that may be chosen to impart specific aesthetic or functional properties to a cushioning element. In one embodiment, apertures 150 may comprise a void that has a substantially cylindrical shape. In some embodiments, the cross-sectional diameter of the aperture may be substantially consistent or uniform throughout the length of the aperture.

In some cases, apertures 150 can be provided on or through lower surface 154 or upper surface 152 of the cushioning element. In other cases, apertures 150 can be provided on or through a side surface of the cushioning element. In one embodiment, apertures 150 can be provided on or through the side surfaces (for example, along first side 156, second side 157, third side 158, and/or fourth side 159) of the cushioning element as well as on lower surface 154 and upper surface 152 of the cushioning element.

In some embodiments, apertures 150 can provide means for decoupling or softening portions of a cushioning element in order to enhance its cushioning characteristics. For purposes of this disclosure, cushioning characteristics refer to the degree of fit, flexibility, cushioning, responsiveness, comfort, resilience, shock absorption, elasticity, and/or stability present in a portion of an element. For example, in some cases, apertures 150 can be formed in side portions and a lower portion of a cushioning element to reduce the cross-sectional profile of the element at particular regions and/or to facilitate increased flexibility between various portions of the element. In one embodiment, apertures 150 can be applied to side portions and an upper portion to form regions between adjacent portions of the element that articulate or bend with respect to one another.

Thus, in the present embodiments, the operation of the cushioning elements can involve providing a material variance in the element. The material variance can be accomplished by providing voids (apertures), which can comprise cut-outs through the cushioning element. As will be described below with respect to FIGS. 20-22, the cut-outs can involve a removal of material from the element, thereby providing softer and/or cushioned regions in the portions that include the apertures.

Generally, apertures 150 can comprise various openings or holes arranged in a variety of orientations and in a variety of locations on or through the cushioning element. For example, as shown in FIG. 1, in some embodiments, a first aperture set 102 may include apertures 150 that extend in a direction generally aligned with vertical axis 170 through thickness 140 of first element 100. In a first cutaway section 104 of first element 100 of FIG. 1, it can be seen that the apertures of first aperture set 102 begin along lower surface 154 and extend toward upper surface 152. Thus, apertures 150 of first aperture set 102 include a series of openings 142 (i.e., gaps or openings) along an exterior surface of first element 100. In FIG. 1, lower surface 154 comprises the exterior surface in which openings 142 (shown here as partially formed in first cutaway section 104) are formed. As will be discussed further below, apertures 150 may extend from an initial hole along an exterior surface to form apertures of varying sizes and lengths through thickness 140 of a cushioning element. Apertures 150 may be blind-hole apertures in some embodiments, where only one end of each of the apertures is open or exposed, while the opposite end of each of the aperture remains enclosed within the thickness of the element (i.e., only one end of each aperture may be exposed on an exterior surface of the element).

Furthermore, in FIG. 2, it can be seen that in another embodiment, there can be a second aperture set 202 comprising apertures 150 that extend in a direction generally aligned with vertical axis 170 through thickness 140 of second element 200. In a second cutaway section 204 of second element 200 of FIG. 2, apertures of second aperture set 202 are formed along upper surface 152 and extend toward lower surface 154. In addition, in FIG. 2, openings 142 that comprise an exposed end of apertures 150 can be seen disposed along upper surface 152.

It should also be understood that in some embodiments of cushioning elements, there may be apertures 150 that are formed along multiple surfaces. For example, in FIG. 3, a third aperture set 302 comprising apertures 150 that extend in a direction generally aligned with vertical axis 170 through thickness 140 of third element 300. However, in this embodiment, as shown in a third cutaway section 304, third aperture set 302 includes apertures 150 with openings 142 formed along both lower surface 154 and upper surface 152. Thus, third aperture set 302 includes an upper set 324 and a lower set 326. Apertures 150 comprising upper set 324 extend from upper surface 152 toward lower surface 154, and apertures 150 comprising lower set 326 extend from lower surface 154 toward upper surface 152.

In another example, as shown in FIG. 4, fourth aperture set 402 may comprise apertures 150 that extend along lateral axis 190 across width 146 of fourth element 400 and/or extend along longitudinal axis 180 across length 148 of fourth element 400. In a fourth cutaway section 404 of fourth element 400, it can be seen that some apertures of fourth aperture set 402 begin along first side 156 and extend toward third side 158. Furthermore, additional apertures 150 begin along second side 157 and extend toward fourth side 159. Thus, similar to the embodiments of FIGS. 1-3, apertures 150 of fourth aperture set 402 include a series of openings 142 along exterior surfaces of fourth element 400. However, in this case, the sidewalls of fourth element 400 also comprise apertures 150.

As described earlier with reference to FIGS. 3 and 4, in some embodiments of cushioning elements, apertures 150 can be formed along multiple surfaces. For example, in FIG. 5, some apertures 150 of a fifth aperture set 502 extend in a direction generally aligned with vertical axis 170 through thickness 140 of fifth element 500, some apertures 150 of fifth aperture set 502 extend along lateral axis 190 through width 146 of fifth element 500, and some apertures 150 of fifth aperture set 502 extend along longitudinal axis 180 through length 148 of fifth element 500. Thus, as shown in a fifth cutaway section 504, fifth aperture set 502 includes apertures 150 with openings 142 formed along both lower surface 154 and upper surface 152, as well as in at least first side 156 and second side 157. In other embodiments, openings 142 may be formed along third side 158 and/or fourth side 159. In some embodiments, openings 142 may only be formed on one side or surface of fifth element 500.

In different embodiments, the number of apertures 150 comprising each set of apertures can vary. For example, in one embodiment, first aperture set 102 can comprise between 1 and 100 apertures, or more than 100 apertures. In another embodiment, first aperture set 102 can comprise between 40 and 70 apertures. In still other embodiments, second aperture set 202 can include more than 100 apertures. In addition, in some embodiments, second aperture set 202 can include between 1 and 30 apertures. In other embodiments, second aperture set 202 can include more than 30 apertures. Similarly, in some embodiments, third aperture set 302, fourth aperture set 402, and/or fifth aperture set 502 can include a wide range of numbers of apertures 150. Thus, depending on the cushioning characteristics desired, there can be more apertures or fewer apertures than illustrated in any set of apertures formed in a portion of a cushioning element.

As noted above, in some embodiments, apertures 150 may extend various distances through a cushioning element. For example, as shown in FIG. 1, some apertures 150 of first aperture set 102 may not extend above a lower portion 184 of first element 100. However, other apertures 150 may extend further upward, above lower portion 184 and into upper portion 182. Likewise, in some cases, apertures 150 of second aperture set 202 may only be disposed in upper portion 182, while other apertures 150 may extend further downward. For example, an aperture may extend from upper surface 152, and be disposed at least partially within lower portion 184. Additionally, in some embodiments, apertures 150 of fourth aperture set 402 may be disposed only within first side portion 186, second side portion 188, forward portion 192, or rear portion 194. However, in other embodiments, apertures may extend further, and be disposed within multiple portions of fourth element 400. It should be understood that the various portions can differ from that shown here and are for reference purposes only. Thus, apertures 150 can include any length from zero to nearly the entire length, width, or height of the cushioning element (including a diagonal length). In cases where the cushioning element varies in geometry from the generally oblong rectangular shape shown in FIGS. 1-5, apertures can be formed such that they extend up to the maximum length, thicknesses, breadth, or width associated with the cushioning element. Thus, in some embodiments, the length of each aperture can vary with the size or dimensions of the cushioning element.

Generally, the shape of one or more apertures 150 in a cushioning element can vary. In some cases, one or more apertures 150 may have a linear configuration or shape. In other cases, one or more apertures 150 may have a nonlinear configuration or shape. In the embodiments of FIGS. 1-5, apertures 150 are shown having a generally linear shape, for example.

In different embodiments, the dimensions of one or more apertures 150 relative to one another can vary. For example, referring to FIG. 1, in some embodiments, the lengths of each aperture in first aperture set 102 can vary. For example, in one embodiment, apertures 150 of first aperture set 102 may be longer than other apertures 150 of first aperture set 102. Thus, in FIG. 1, a first aperture 110 has a smaller length than adjacent second aperture 112. In other cases, however, the lengths of each aperture in first aperture set 102 can vary in another manner. First aperture 110 may have a length that is substantially similar to or greater than the length of second aperture 112, for example. Thus, each aperture can have a length that differs from the length of other apertures, and apertures 150 located in different portions of a cushioning element can vary in length relative to one another. The length of an aperture can also vary with reference to longitudinal axis 180 and/or lateral axis 190 (as in fourth aperture set 402). Some examples of this variety will be described further below.

Additionally, the size of each aperture can vary. For purposes of this description, the size of an aperture can refer to the cross-sectional diameter or size of an aperture. In some cases, the volume associated with the interior of an aperture can be correlated with the average cross-sectional diameter of the aperture. Referring to FIG. 3, in some cases, each aperture in third aperture set 302 can have a substantially similar size (e.g., cross-sectional diameter). In other cases, two or more apertures in third aperture set 302 can have substantially different sizes. For example, a third aperture 310 has a size that is smaller than the size of adjoining fourth aperture 312. In other cases, however, the sizes of each aperture in third aperture set 302 can vary in another manner. Third aperture 310 may have a size that is substantially similar to or greater than the size of fourth aperture 312, for example. Thus, each aperture can have a size that differs from the size of other apertures, and apertures 150 located in different portions of a cushioning element can vary in size relative to one another. In other cases, the size of each aperture can vary with the size of the cushioning element. It should be understood that the size of an aperture can vary throughout a single aperture, such that one region of an aperture is larger or smaller than another region of the same aperture. However, in other embodiments, the size of an aperture may remain substantially constant throughout the length of the aperture. Some examples of this variety will be described further below.

In some embodiments, apertures on different portions of a cushioning element can be generally parallel with one another with respect to another surface or side of the element. In some cases, apertures extending from the same surface of a cushioning element may be generally parallel with one another, such that they do not intersect. In other words, the apertures may be generally oriented in a similar direction. For example, apertures formed on lower surface 154 or upper surface 152 may be similarly oriented in a direction generally aligned with vertical axis 170. Thus, in different embodiments, apertures 150 may be associated with approximately similar longitudinal, lateral, or vertical orientations. In other embodiments, however, apertures on the side surfaces may not be parallel with one another. In one example, there may be apertures with openings 142 on first side 156 that are oriented in one direction, and apertures with openings 142 on first side 156 that are oriented along a different direction. Furthermore, it will be understood that in some embodiments, only some apertures may be generally aligned through upper portion 182, lower portion 184, first side portion 186, second side portion 188, forward portion 192, and/or rear portion 194, while other apertures disposed throughout the cushioning element may not be aligned. Therefore, it should be understood that while the embodiments of FIGS. 1-5 show apertures 150 having lengths extending along either vertical axis 170, longitudinal axis 180, or lateral axis 190, apertures can also be oriented so that they lie along any other direction (e.g., a diagonal or non-planar direction). For example, in some embodiments, apertures can form an angle less than 90 and greater than 0 degrees with respect to vertical axis 170, lateral axis 190, and/or longitudinal axis 180. In some cases, apertures can form an angle between 30 and 60 degrees with respect to vertical axis 170, lateral axis 190, and/or longitudinal axis 180.

Referring to FIG. 4, some apertures of fourth aperture set 402 (such as those apertures that have openings 142 formed along first side 156) may also be positioned to be aligned with another aperture of fourth aperture set 402 (such as with an aperture that has a hole formed along third side 158). In another embodiment, an aperture with a hole formed along second side 157 may be approximately aligned with an aperture that has a hole formed along fourth side 159. It will be understood that the approximate alignment between some apertures refers to an approximately similar arrangement for these apertures along vertical axis 170, longitudinal axis 180, or lateral axis 190. For example, in the embodiment of FIG. 3, a fifth aperture 320 formed on upper surface 152 is approximately aligned with a sixth aperture 322 formed on lower surface 154.

In a similar manner, one or more apertures of third aperture set 302, fourth aperture set 402, or fifth aperture set 502 may be approximately aligned with other apertures that have openings 142 disposed on the opposite surface. In other embodiments, however, apertures within a set may not be aligned with other apertures in the set. In addition, in some cases, only some apertures may be aligned. In particular, in embodiments where there are a greater number of apertures on one side than along the opposite side, it may not be possible to align all of the apertures.

As a result of the inclusion of different possible configurations of apertures 150, a cushioning element may have varying responsiveness to forces. In other words, apertures 150 can be disposed in a pattern that can help attenuate ground reaction forces and absorb energy, imparting different cushioning characteristics to the element. In the embodiments of FIGS. 6-14, a sequence of images representing possible responses of the cushioning elements under a load are shown.

Figure 6:
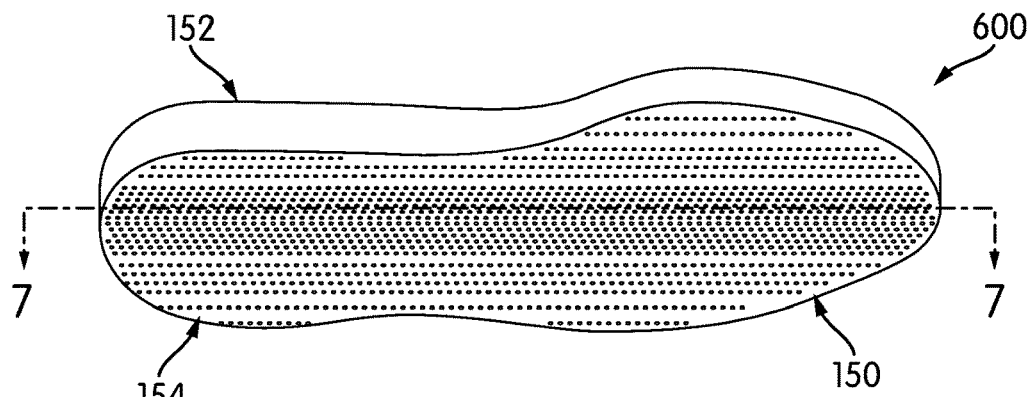
FIG. 6 is an isometric bottom view of an embodiment of a sole member comprising a cushioning element.
Figure 7:
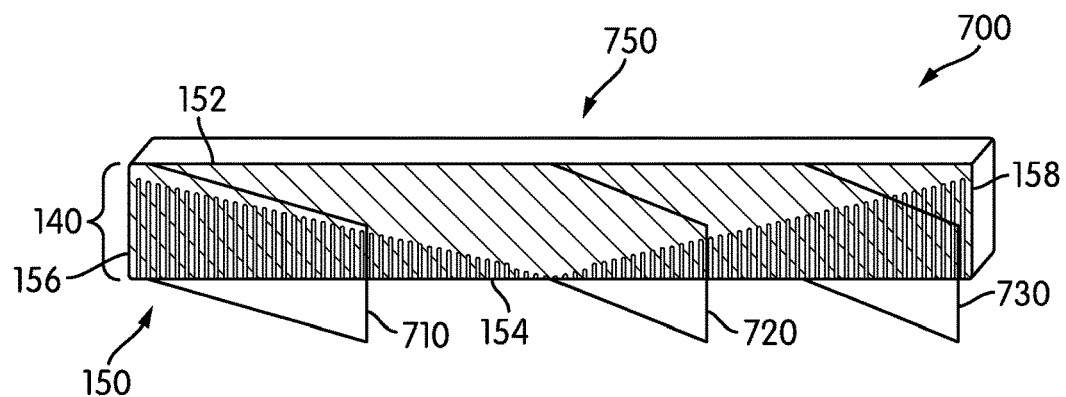
FIG. 7 is an isometric view of an embodiment of a cushioning element including apertures in an unloaded state.
Figure 8:
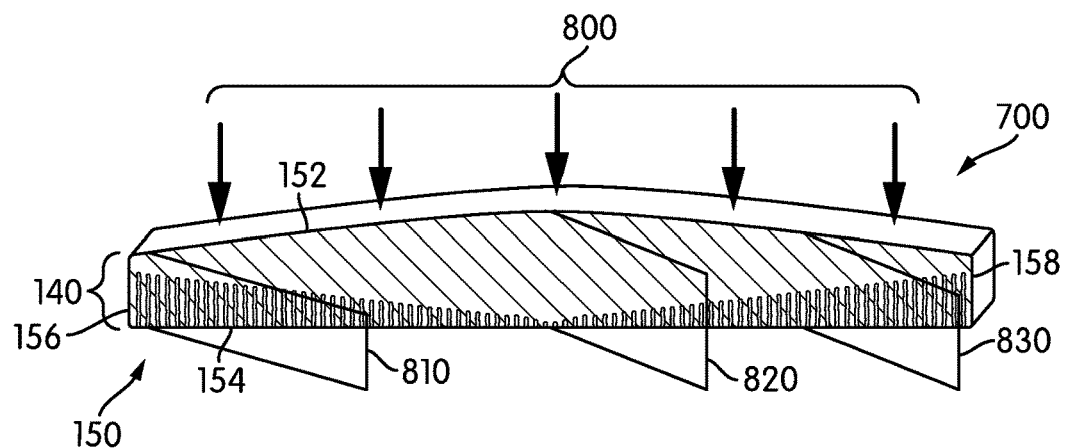
FIG. 8 is an isometric view of an embodiment of a cushioning element including apertures experiencing deformation.

For purposes of providing a contextual example to the reader, FIG. 6 depicts an embodiment of a first sole member 600. In FIG. 7, a cross section taken along the line 7-7 of FIG. 6 in first sole member 600 is shown, depicting a sixth element 700. Sixth element 700 has a series of apertures 150 disposed along lower surface 154 and extending through thickness 140 at varying lengths. For example, apertures 150 disposed nearer to third side 158 are longer than apertures 150 disposed nearer to a center 750 of sixth element 700. Furthermore, apertures 150 disposed nearer to center 750 of sixth element 700 are smaller than apertures 150 disposed closer to first side 156. In some embodiments, apertures 150 may form a progression pattern. For purposes of this disclosure, a progression pattern refers to a succession or series pattern, where there is a movement or change toward a greater or lesser length or size. In some embodiments, the progression can be gradual, or occur in stages. In one embodiment, a gradual progression is one where the length of an aperture between two adjacent apertures has a value equal to or between the two lengths of the adjacent apertures. In some embodiments, the progression may be mathematical. In one embodiment, the progression may be approximately linear. In another embodiment, the progression may be approximately geometric. In some embodiments, the progression may be approximately trigonometric. For example, in one embodiment, the progression may be approximately sinusoidal. In some embodiments, apertures 150 may be arranged such that there is a generally predictable rise and fall to the heights of the apertures throughout the cushioning element. Thus, in some embodiments, apertures 150 may be "tuned" to provide a smooth feel to the cushioning element, and improve comfort for a user. In FIGS. 7-8, apertures 150 decrease in length as they approach center 750 of sixth element 700, and then increase in length as they move further away from center 750. A regular arrangement as shown in sixth element 700 may provide more consistent cushioning for a user in some cases. However, it should be understood that, in other embodiments, apertures 150 may have a random height arrangement.

For purposes of convenience, heights can be associated with different portions of sixth element 700. In FIG. 7, a first height 710, a second height 720, and a third height 730 are identified. First height 710 is associated with the portion of sixth element 700 toward first side 156, second height 720 is associated with the portion of sixth element 700 toward center 750, and third height 730 is associated with the portion of sixth element 700 toward third side 158. In FIG. 7, first height 710, second height 720, and third height 730 are substantially similar, such that thickness 140 is generally uniform throughout sixth element 700.

When sixth element 700 undergoes a first load 800 (represented by arrows), as shown in FIG. 8, the arrangement of apertures 150 can alter the cushioning responsiveness of the material. In FIG. 8, first load 800 is directed downward in a direction generally aligned with vertical axis 170 and distributed in a substantially constant or uniform manner over upper surface 152 of sixth element 700. As sixth element 700 experiences the force of first load 800, sixth element 700 can deform.

In some embodiments, when cushioning elements are compressed, they can deform in different ways. The deformation that occurs can be related to the location of any apertures, and/or the size and orientation of the apertures. Thus, apertures 150 may function together within the material of the cushioning element to provide variations in the relative stiffness, degree of ground reaction force attenuation, and energy absorption properties of the cushioning element. These cushioning characteristics may be altered to meet the specific demands of the activity for which the cushioning element is intended to be used, through the methods described herein.

In some embodiments, when the compressive force of first load 800 is applied to sixth element 700, for example, the areas that include more apertures and/or apertures of greater size or length may deform to a greater extent than the portions of sixth element 700 that have fewer apertures and/or apertures of smaller size or length. As a result of the application of first load 800, the aperture openings can be compressed and/or deformed, as shown in FIG. 8. In the region nearest to third side 158, where there are longer apertures relative to the center of sixth element 700, the deformation is greater. Similarly, in the region nearest to first side 156, where the apertures are longer relative to the apertures toward center 750, the degree of deformation is greater. Thus, the least deformation of sixth element 700 occurs near center 750, where there are shorter or smaller apertures.

In some embodiments, the deformation that occurs throughout sixth element 700 can be measurable in part by the changed shape and height of sixth element 700 and/or the changed shape and heights of apertures 150. Specifically, in FIG. 8, a fourth height 810, a fifth height 820, and a sixth height 830 are identified. Fourth height 810 is associated with the portion of sixth element 700 toward first side 156, fifth height 820 is associated with the portion of sixth element 700 toward center 750 of sixth element 700, and sixth height 830 is associated with the portion of sixth element 700 toward third side 158. Referring to FIGS. 7 and 8, as a result of first load 800, it can be seen that fourth height 810 is less than first height 710, fifth height 820 is less than second height 720, and sixth height 830 is less than third height 730. Furthermore, in FIG. 8, fourth height 810, fifth height 820, and sixth height 830 are substantially different from one another, such that thickness 140 is generally non-uniform throughout sixth element 700. In other words, various contours have been formed along upper surface 152 where first load 800 has been applied. The contours may vary in a manner generally corresponding to the arrangement of apertures 150 disposed in sixth element 700 in some embodiments. Thus, fifth height 820 is greater than either fourth height 810 or sixth height 830, and sixth height 830 is greater than fourth height 810.

In some embodiments, the shape or orientation of the apertures may also change as a result of an applied force. Depending on the magnitude and the direction of the force(s) applied, the changes in area or shape may vary. For example, referring to FIG. 8, in one embodiment, sixth element 700 may be exposed to a force or load whereby apertures become deformed not only by becoming more compact, but also by curling or otherwise becoming increasingly non-linear and/or irregular. In one embodiment, the area or volume of an aperture may decrease when a compressive force is applied.

Figure 9:
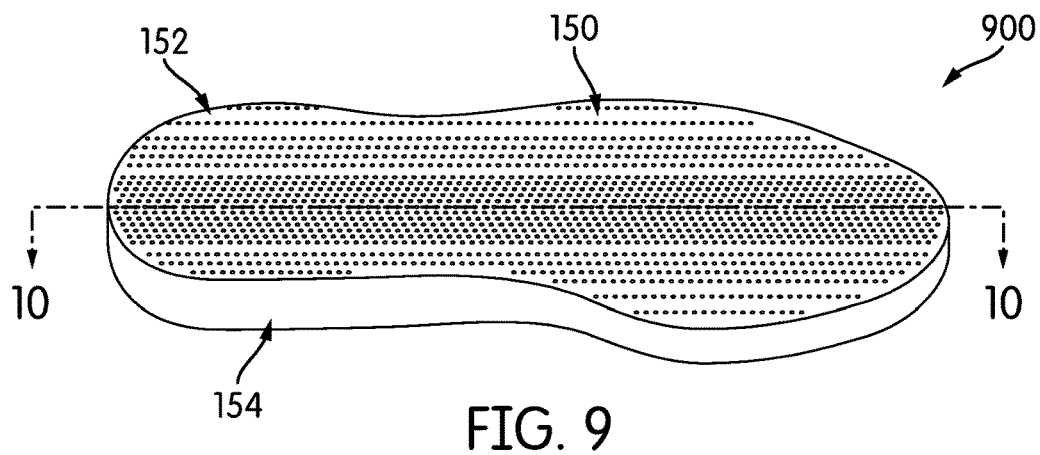
FIG. 9 is an isometric top view of an embodiment of a sole member comprising a cushioning element.
Figure 10:
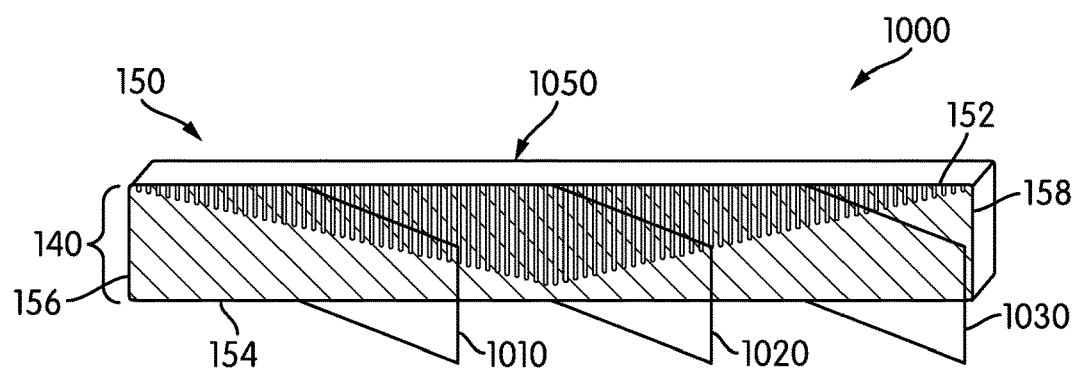
FIG. 10 is an isometric view of an embodiment of a cushioning element including apertures in an unloaded state.

Similarly, compressive forces can produce responses in other types of cushioning elements. For purposes of providing a contextual example to the reader, FIG. 9 depicts an embodiment of a second sole member 900. In FIG. 10, a cross section taken along the line 10-10 of FIG. 9 in second sole member 900 depicts an unloaded seventh cushioning element ("seventh element") 1000. Seventh element 1000 has a series of apertures 150 disposed along lower surface 154 and extending through thickness 140 at varying lengths. In FIG. 10, apertures 150 disposed nearer to third side 158 are smaller than apertures 150 disposed nearer toward a center 1050 of seventh element 1000. Furthermore, apertures 150 disposed nearer to first side 156 are also smaller than apertures 150 disposed nearer toward center 1050. For purposes of convenience, heights are associated with different portions of seventh element 1000. In FIG. 10, a seventh height 1010, an eighth height 1020, and a ninth height 1030 are identified. Seventh height 1010 is associated with the portion of seventh element 1000 toward first side 156, eighth height 1020 is associated with the portion of seventh element 1000 toward center 1050, and ninth height 1030 is associated with the portion of seventh element 1000 toward third side 158. In FIG. 10, seventh height 1010, eighth height 1020, and ninth height 1030 are substantially similar, such that thickness 140 is generally uniform throughout seventh element 1000.

Figure 11:
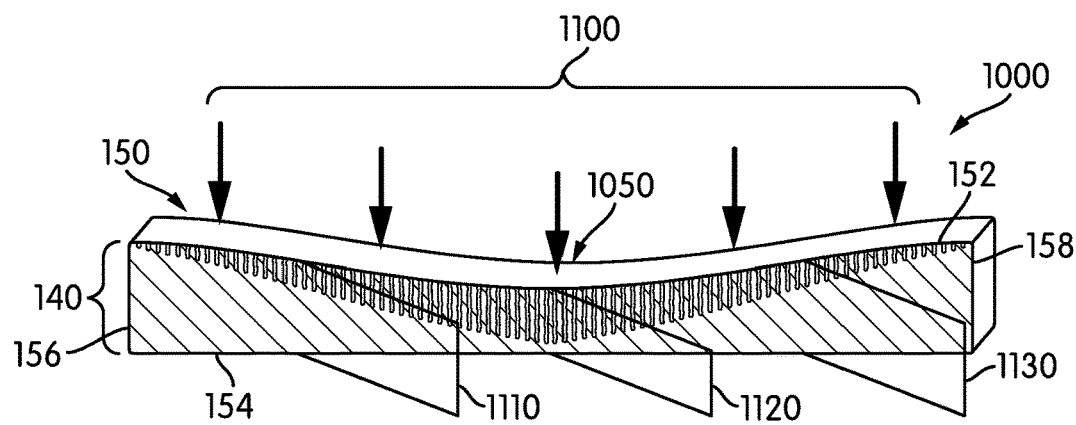
FIG. 11 is an isometric view of an embodiment of a cushioning element including apertures experiencing deformation.

However, when seventh element 1000 undergoes a second load 1100 (represented by arrows), as shown in FIG. 11, the arrangement of apertures 150 can alter the responsiveness of the material. In FIG. 11, second load 1100 is directed downward in a direction generally aligned with vertical axis 170 and distributed in a substantially constant, uniform manner over upper surface 152 of seventh element 1000. As seventh element 1000 experiences the force of second load 1100, seventh element 1000 can deform, as described above with respect to FIGS. 7 and 8.

When the compressive force of second load 1100 is applied to seventh element 1000, for example, the areas that include more apertures and/or apertures of greater size or length may deform to a greater extent than the portions of seventh element 1000 that have fewer apertures and/or apertures of smaller size or length. As a result of the application of second load 1100, the aperture openings may be compressed and deformed. In the region toward center 1050, where the apertures are larger relative to other apertures, the degree of deformation is greater. In the regions nearest third side 158 and first side 156, where there are smaller apertures (relative to center 1050 of seventh element 1000), the deformation is not as great.

In some embodiments, the deformation that occurs throughout seventh element 1000 can be measurable in part by the changed shape and height of seventh element 1000 and/or the changed shape and heights of apertures 150. In FIG. 11, a tenth height 1110, an eleventh height 1120, and a twelfth height 1130 can be identified. Tenth height 1110 is associated with the portion of seventh element 1000 toward first side 156, eleventh height 1120 is associated with the portion of seventh element 1000 toward center 1050, and twelfth height 1130 is associated with the portion of seventh element 1000 toward third side 158. Thus, referring to FIGS. 10 and 11, in response to second load 1100, tenth height 1110 is less than seventh height 1010, eleventh height 1120 is less than eighth height 1020, and twelfth height 1130 is less than ninth height 1030. Furthermore, the heights across seventh element 1000 can differ, such that thickness 140 is generally non-uniform throughout seventh element 1000. In other words, various contours can be formed along upper surface 152 where second load 1100 has been applied.

The contours may vary in a manner generally corresponding to the arrangement of apertures 150 disposed in seventh element 1000 in some embodiments. Thus, if apertures 150 are arranged in a repeating pattern, as seen with the apertures associated with first side 156 and the apertures associated with third side 158, which are arranged in a "mirrored" configuration, the deformation that occurs can be similarly mirrored, and the change in height may also reflect this mirroring. Thus, while eleventh height 1120 is less than either tenth height 1110 or twelfth height 1130, tenth height 1110 and twelfth height 1130 may be substantially similar. In other words, while some areas can be provided with different cushioning properties relative to other areas, there may also be areas that are provided with similar cushioning properties. This was also depicted in FIGS. 8 and 9.

Figure 12:
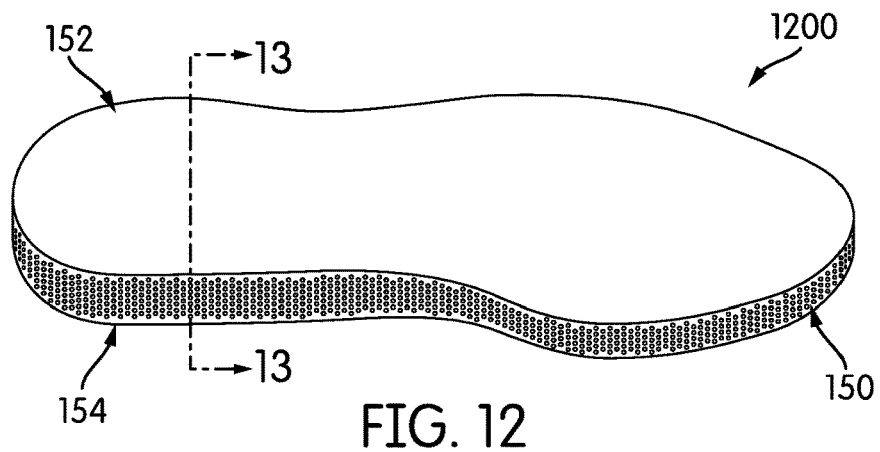
FIG. 12 is an isometric top view of an embodiment of a sole member comprising a cushioning element.
Figure 13:
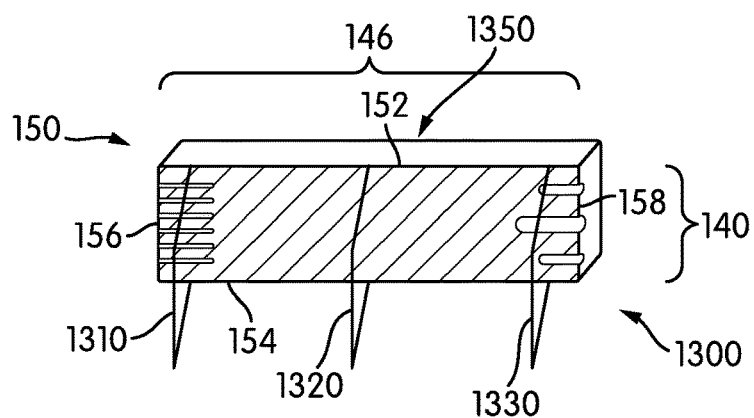
FIG. 13 is an isometric view of an embodiment of a cushioning element including apertures in an unloaded state.

Likewise, compressive forces can produce responses in other cushioning elements. For purposes of providing a contextual example to the reader, FIG. 12 depicts an embodiment of a third sole member 1200. In FIG. 13, a cross section taken along the line 13-13 of FIG. 12 in third sole member 1200 depicts an unloaded eighth cushioning element ("eighth element") 1300. Eighth element 1300 has a series of apertures 150 disposed along the sidewall surfaces of the element. In other words, the apertures extend in a generally horizontal direction (e.g., a direction generally aligned with lateral axis 190 or a direction generally aligned with longitudinal axis 180) through first side 156 and third side 158, as described earlier with respect to FIGS. 4 and 5.

Thus, apertures 150 in eighth element 1300 are disposed such that they extend through width 146 at varying lengths. Furthermore, in FIG. 13, apertures 150 disposed along third side 158 are larger than apertures 150 disposed along first side 156 of eighth element 1300. In other words, apertures 150 that extend toward a center 1350 from first side 156 are narrower than the apertures that extend toward center 1350 from third side 158. In addition, no apertures are disposed within the portion associated with center 1350 of eighth element 1300.

For purposes of convenience, heights are associated with different portions of eighth element 1300. In FIG. 13, a thirteenth height 1310, a fourteenth height 1320, and a fifteenth height 1330 are identified. Thirteenth height 1310 is associated with the portion of eighth element 1300 disposed proximate first side 156, fourteenth height 1320 is associated with the portion of eighth element 1300 disposed proximate center 1350, and fifteenth height 1330 is associated with the portion of eighth element 1300 disposed proximate third side 158. In FIG. 13, thirteenth height 1310, fourteenth height 1320, and fifteenth height 1330 are substantially similar, such that thickness 140 is generally uniform throughout eighth element 1300.

Figure 14:
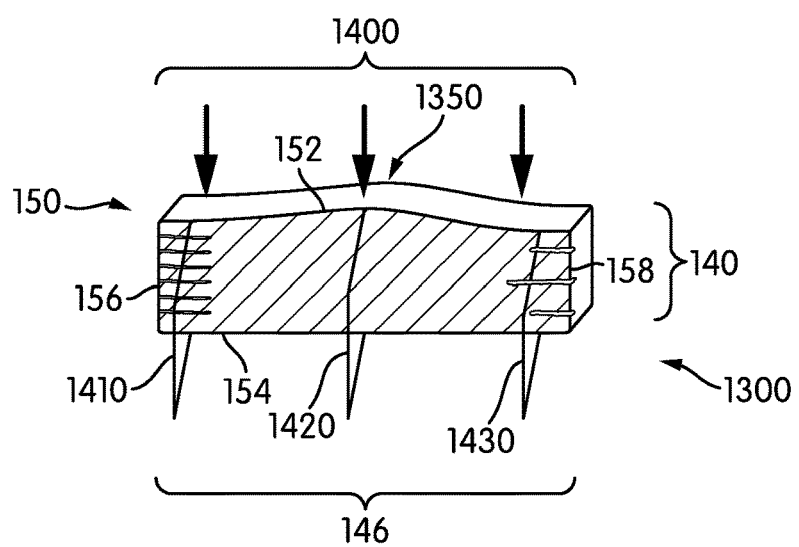
FIG. 14 is an isometric view of an embodiment of a cushioning element including apertures experiencing deformation.

However, when eighth element 1300 undergoes a third load 1400 (represented by arrows), as shown in FIG. 14, the arrangement of apertures 150 can alter the responsiveness of the material. In FIG. 14, third load 1400 is directed downward in a direction generally aligned with vertical axis 170 and distributed in a substantially constant manner over upper surface 152 of eighth element 1300. As eighth element 1300 experiences the force of third load 1400, eighth element 1300 can deform, as described above with respect to FIGS. 7-11.

When the compressive force of third load 1400 is applied to eighth element 1300, for example, the areas that include more apertures and/or apertures of greater size or length may deform to a greater extent than the portions of eighth element 1300 that have apertures of smaller size. As a result of the application of third load 1400, the aperture openings can be compressed and/or deformed. In the region toward center 1350, where there are no apertures, the degree of deformation can be minimal relative to other areas that include apertures. Thus, in the regions nearest third side 158 and first side 156, where there are apertures (relative to center 1350 of eighth element 1300), the deformation is more significant. Furthermore, as the apertures nearest third side 158 are larger than the apertures nearest first side 156, there may be further differences in how eighth element 1300 responds to third load 1400.

In FIG. 14, a sixteenth height 1410, a seventeenth height 1420, and an eighteenth height 1430 can be identified. Sixteenth height 1410 is associated with the portion of eighth element 1300 toward first side 156, seventeenth height 1420 is associated with the portion of eighth element 1300 along center 1350, and eighteenth height 1430 is associated with the portion of eighth element 1300 toward third side 158. Referring to FIGS. 13 and 14, as a result of third load 1400, sixteenth height 1410 is less than thirteenth height 1310, seventeenth height 1420 is less than fourteenth height 1320, and eighteenth height 1430 is less than fifteenth height 1330. Furthermore, similar to sixth element 700 and seventh element 1000, the heights across eighth element 1300 can differ, such that thickness 140 is generally non-uniform throughout eighth element 1300. In other words, various contours can be formed along upper surface 152 where third load 1400 has been applied. The contours can vary in a manner generally corresponding to the arrangement of apertures 150 disposed in eighth element 1300 in some embodiments. In FIG. 14, seventeenth height 1420 is greater than either sixteenth height 1410 or eighteenth height 1430. In addition, sixteenth height 1410 may be greater than eighteenth height 1430, as apertures associated with the region corresponding to sixteenth height 1410 are substantially more narrow than the apertures in the region corresponding to eighteenth height 1430.

Thus, exposure to various forces may also produce a change in the shape or geometry, size, and/or height of cushioning elements and the apertures that may be disposed within the cushioning element. It should be understood that while first load 800, second load 1100, and third load 1400 are shown as being generally uniform, other loads may be non-uniform. Depending on the magnitude and the direction of the force(s) applied, changes in area, volume, dimensions, and/or shape of the cushioning element may vary. In some embodiments, a different force may permit the cushioning element to expand in a lateral or longitudinal direction, such that the overall length of the element increases. In other embodiments, different forces may alter the responses of the cushioning element.

It should be noted that the various degrees of deformation described and shown here are for purposes of illustration. In some situations, the cushioning element may not undergo compression to the extent depicted, or may deform more or less, depending on various factors such as the materials used in the production of the cushioning element, as well as its incorporation in other objects or articles. For example, if a cushioning element is joined or attached to a less reactive material, the compressive and/or expansive properties described herein may differ, or be limited. In some embodiments, when the cushioning element is joined to a strobel or other structure, the capacity of expansion may decrease. In some embodiments, the perimeter of the cushioning element may be fixed, e.g., bonded to a strobel layer or another sole layer. However, in such embodiments, the cushioning characteristics of the cushioning element may still facilitate increased flexibility and cushioning.

Furthermore, it should be understood that while sixth element 700, seventh element 1000, and eighth element 1300 may experience various forces and deformation, the deformation may be elastic. In other words, once the load is removed or decreased, the cushioning element may recover and return to its original dimensions and/or shape, or to dimensions and/or a shape substantially similar to the original, unloaded configuration.

As noted above, the cushioning elements described herein may be utilized with various components or articles. For example, the degree of elasticity, cushioning, and flexibility of a sole component such as a sole member can be important factors associated with comfort and injury prevention for an article of footwear. FIGS. 15-18 depict an embodiment of a method of designing a customized sole member for an article of footwear.

Figure 15:
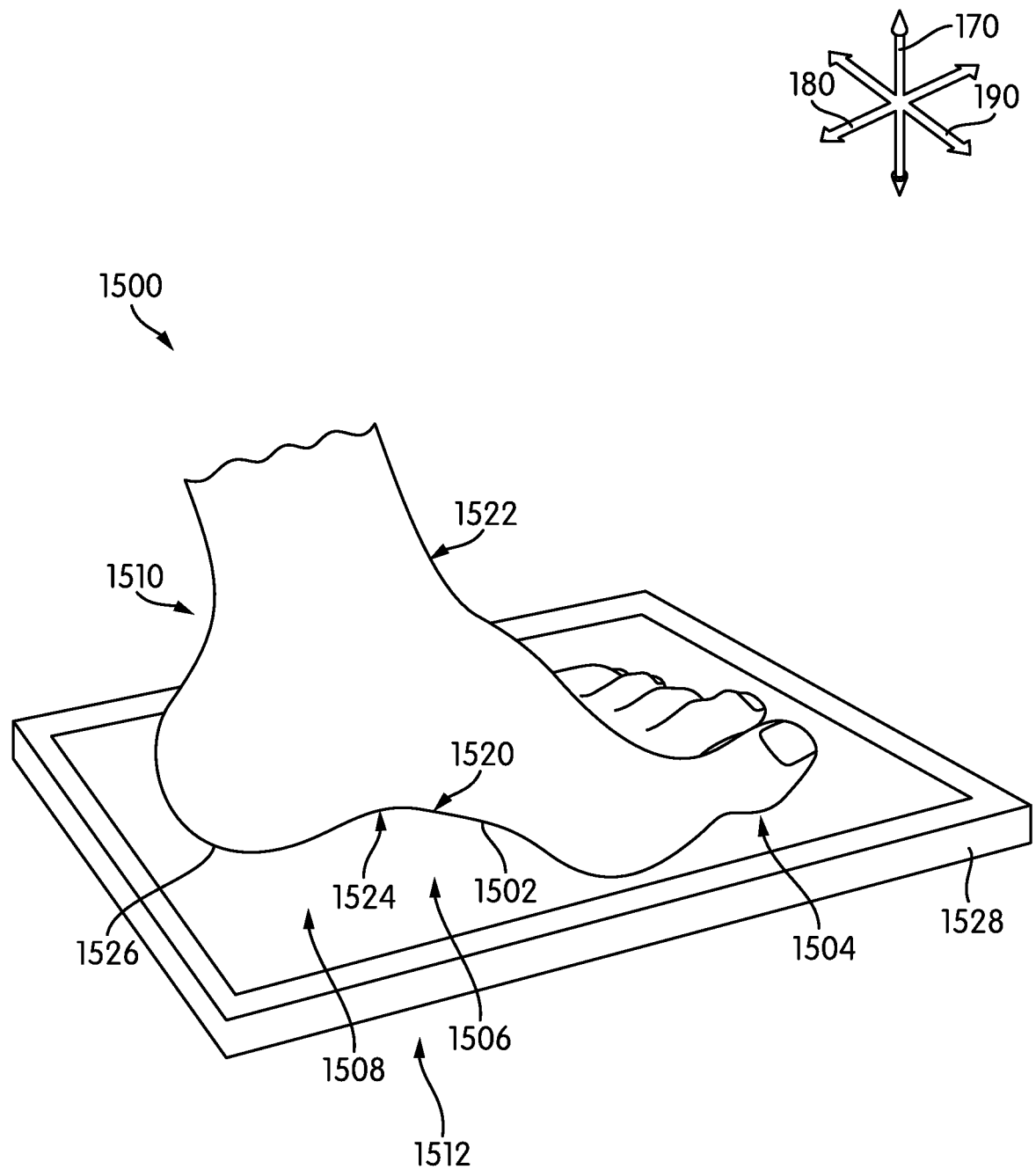
FIG. 15 illustrates an embodiment of the use of a device for obtaining three-dimensional foot data.

FIG. 15 shows the three-dimensional shape of a plantar surface 1502 of a foot 1500 being measured using a data collection apparatus 1528. In some cases, data collection apparatus 1528 can be a force platform. In other cases, data collection apparatus 1528 can comprise one of the commercially available systems for measuring plantar pressure (e.g., Emed sensor platform, Pedar insole system, F-Scan system, Musgrave footprint system, etc.). Plantar pressure measurement systems can provide a means of obtaining specialized information regarding a foot that can be used to customize footwear for individuals. In some embodiments, the magnitude of pressure can be determined by dividing the measured force by the known area of the sensor or sensors evoked while the foot was in contact with the supporting surface in some embodiments.

For purposes of reference, foot 1500, representations of foot 1500, components associated with foot 1500 (such as an article of footwear, an upper, a sole member, a computer-aided design of foot 1500, and other components/representations) may be divided into different regions. Foot 1500 may include a forefoot region 1504, a midfoot region 1506 and a heel region 1508. Forefoot region 1504 may be generally associated with the toes and joints connecting the metatarsals with the phalanges. Midfoot region 1506 may be generally associated with the metatarsals of a foot. Heel region 1508 may be generally associated with the heel of a foot, including the calcaneus bone. In addition, foot 1500 may include a lateral side 1510 and a medial side 1512. In particular, lateral side 1510 and medial side 1512 may be associated with opposing sides of foot 1500. Furthermore, both lateral side 1510 and medial side 1512 may extend through forefoot region 1504, midfoot region 1506, and heel region 1508. It will be understood that forefoot region 1504, midfoot region 1506, and heel region 1508 are only intended for purposes of description and are not intended to demarcate precise regions of foot 1500. Likewise, lateral side 1510 and medial side 1512 are intended to represent generally two sides of foot 1500, rather than precisely demarcating foot 1500 into two halves.

Figure 16:
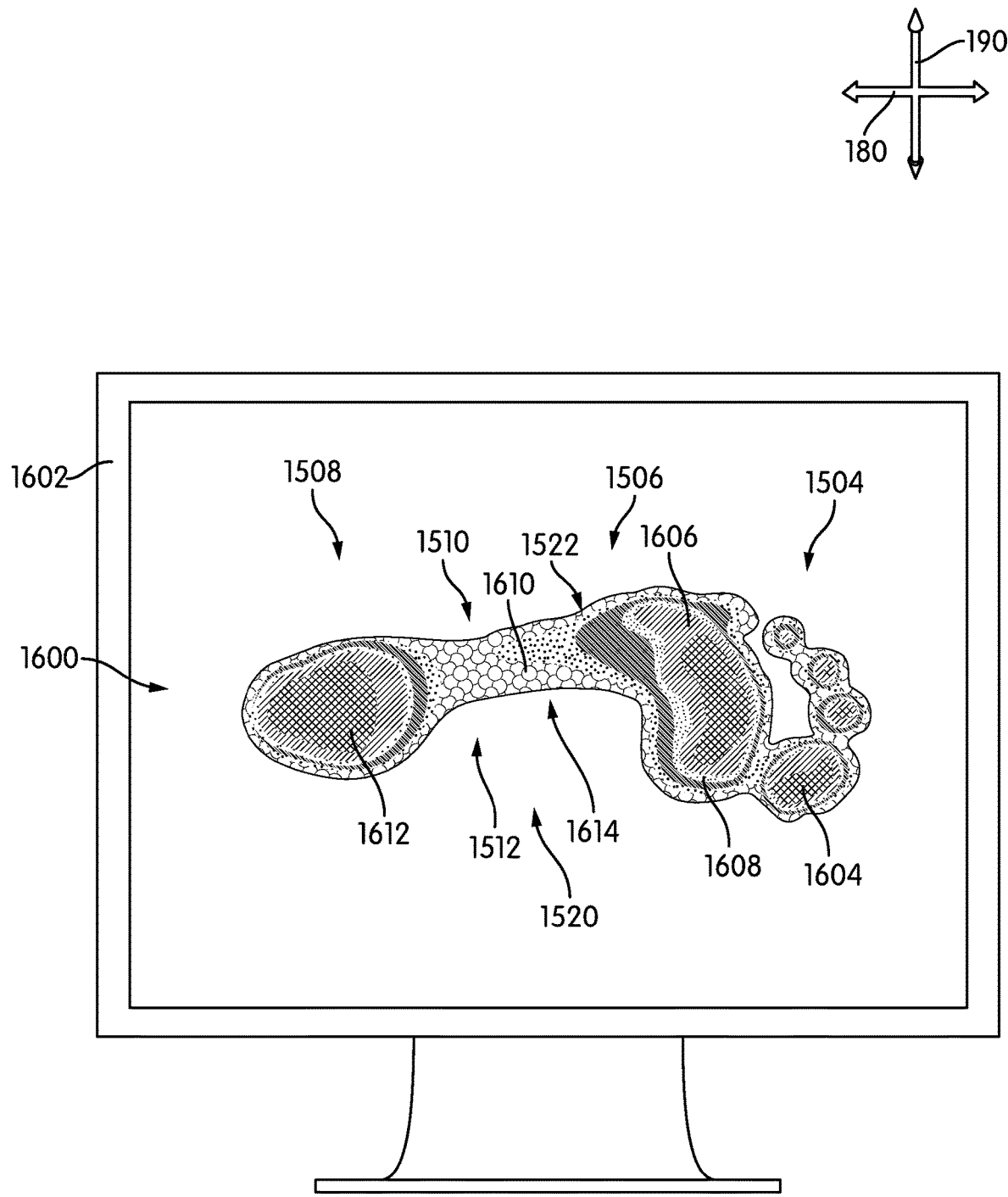
FIG. 16 schematically illustrates an embodiment of a virtual image of digitized three-dimensional foot data.

Furthermore, in the examples depicted in FIGS. 15 and 16, foot 1500 and/or a virtual scan 1600 of a foot may include a medial arch area 1520, associated with an upward curve along medial side 1512 of midfoot region 1506, and a lateral arch area 1522, associated with an upward curve along lateral side 1510 of midfoot region 1506. The region corresponding to lateral arch area 1522 is best seen in FIG. 16, which illustrates a computer screen or virtual image of digitized three-dimensional foot data. As described below, the curvature of medial arch area 1520 and lateral arch area 1522 may vary from one foot to another. In addition, foot 1500 includes a transverse arch 1524 that extends along lateral axis 190 near forefoot region 1504 along plantar surface 1502. Foot 1500 also includes a heel prominence 1526, which is the prominence located in heel region 1508 of foot 1500. As shown in FIG. 15, foot 1500 is illustrated as a left foot; however, it should be understood that the following description may equally apply to a mirror image of a foot or, in other words, a right foot.

Although the embodiments throughout this detailed description depict components configured for use in athletic articles of footwear, in other embodiments, the components may be configured to be used for various other kinds of footwear including, but not limited to, hiking boots, soccer shoes, football shoes, sneakers, running shoes, cross-training shoes, rugby shoes, basketball shoes, baseball shoes as well as other kinds of shoes. Moreover, in some embodiments, components may be configured for various kinds of non-sports related footwear, including, but not limited to, slippers, sandals, high-heeled footwear, loafers as well as any other kinds of footwear.

Components associated with an article of footwear are generally made to fit various sizes of feet. In the embodiments shown, the various articles are configured with approximately the same footwear size. In different embodiments, the components could be configured with any footwear size, including any conventional sizes for footwear known in the art. In some embodiments, an article of footwear may be designed to fit the feet of a child. In other embodiments, an article of footwear may be designed to fit the feet of an adult. Still, in other embodiments, an article of footwear may be designed to fit the feet of a man or a woman.

Referring to FIGS. 15 and 16, a first step of the present method is to collect data related to foot 1500, such as using a barefoot pressure measurement or other data, from the foot being measured on data collection apparatus 1528. Data collection apparatus 1528 may include provisions for capturing information about an individual's feet. Specifically, in some embodiments, data collection apparatus 1528 may include provisions to capture geometric information about one or more feet. This geometric information can include size (e.g., length, width, and/or height) as well as three-dimensional information corresponding to the customer's feet (e.g., forefoot geometry, midfoot geometry, heel geometry, and ankle geometry). In at least one embodiment, the captured geometric information for a customer's foot can be used to generate a three-dimensional model of the foot for use in later stages of manufacturing. In particular, the customized foot information can include at least the width and length of the foot. In some cases, the customized foot information may include information about the three-dimensional foot geometry. Customized foot information can be used to create a three-dimensional model of the foot. Embodiments may include any other provisions for capturing customized foot information. The present embodiments could make use of any of the methods and systems for forming an upper disclosed in Bruce, U.S. patent application Ser. No. 14/565,582, filed Dec. 10, 2014, titled "Portable Manufacturing System for Articles of Footwear," the entirety of which is herein incorporated by reference.

Some embodiments could use any of the systems, devices, and methods for imaging a foot as disclosed in Leedy et al., U.S. Patent Publication Number 2013/0258085, published Oct. 3, 2013, and titled "Foot Imaging and Measurement Apparatus," (previously U.S. patent application Ser. No. 13/433,463, filed Mar. 29, 2012), the entirety of which is herein incorporated by reference.

In FIG. 16, a screen 1602 displays virtual scan 1600 of plantar pressure distributions for foot 1500. Virtual scan 1600 may provide a measured foot image or representation, including various distinct regions to indicate the pressures applied or experienced by foot 1500 over its plantar surface 1502. In one example, pressures can include a first pressure area 1604, a second pressure area 1606, a third pressure area 1608, a fourth pressure area 1610, and a fifth pressure area 1612. An additional pressure area 1614 is indicated where plantar surface 1502 did not make an impressionable contact with the surface of data collection apparatus 1528. In some embodiments, colors (not shown in FIG. 16) can be included in virtual scan 1600 to more readily distinguish variations within the measured pressure data. It should be noted that in other embodiments, different, fewer, or more pressure areas may be measured or indicated.

As seen in FIG. 16, in some embodiments, the data collected may include scan 1600 of foot 1500. In some embodiments, scan 1600 may be used to assess the three-dimensional shape and obtain digital data in a two-dimensional or a three-dimensional reference frame. In other embodiments, scan 1600 can provide a baseline shape for a footwear component. In one embodiment, three-dimensional scanned images may be used to measure the overall shape of a person's feet, and obtain two-dimensional measurements such as an outline, length, and width of foot 1500. Obtaining foot geometry can establish a baseline record for the person in one embodiment. In some embodiments, other input may also be provided to supplement information regarding the person being measured. In different embodiments, additional data such as toe height information may also be obtained. In other embodiments, plaster casts of a person's foot may be taken and digitized. Additionally, other digital or imaging techniques that may be employed to capture two- and three-dimensional foot shape and profile can be used to construct and/or supplement scan 1600. In other embodiments, the person whose foot is being measured may provide answers to questions describing the person's physical characteristics, limitations, preferences, and/or personal lifestyle, which may impact the design of the various parts described herein.

Figure 17:
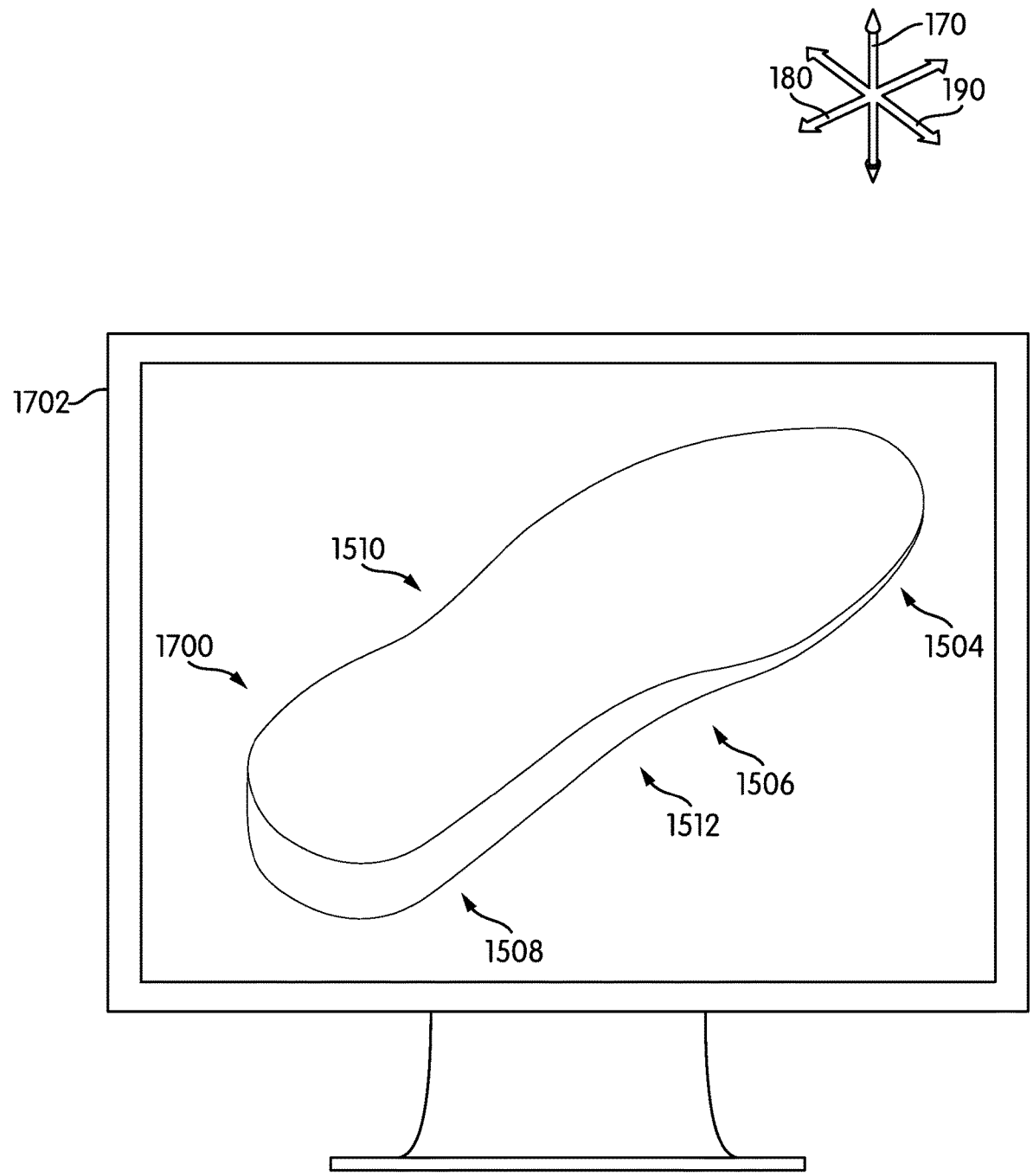
FIG. 17 schematically illustrates an embodiment of a virtual image of a template for a sole member.
Figure 18:
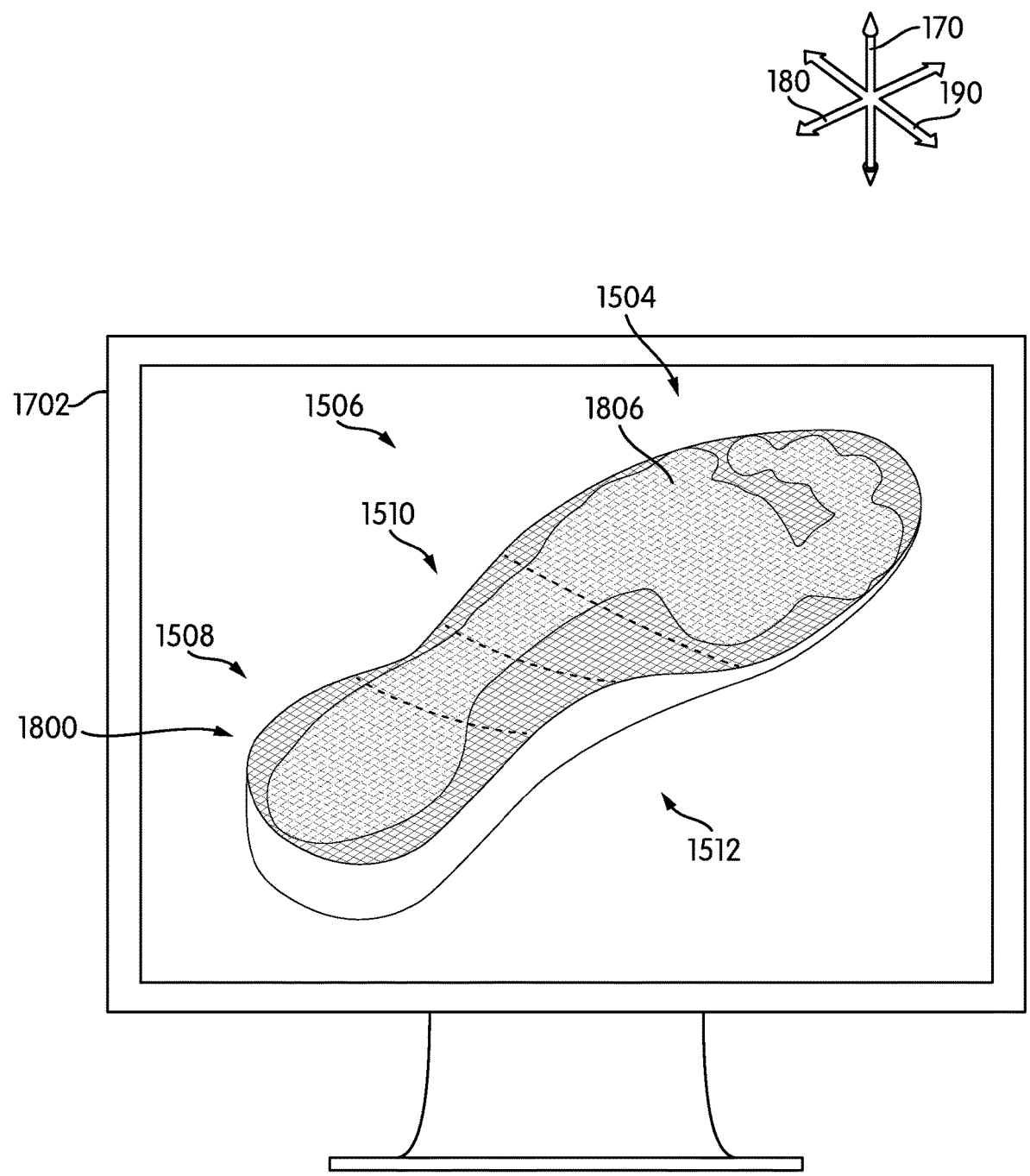
FIG. 18 schematically illustrates an embodiment of a virtual image of a customized sole member.

In different embodiments, a sole member may provide one or more functions for an article of footwear. In FIG. 17, an image of a template of a sole member 1700 is displayed on a screen 1702. In some embodiments, sole member 1700 may attenuate ground reaction forces when compressed between the foot and the ground during walking, running, or other ambulatory activities. The configuration of sole member 1700 may vary significantly in different embodiments to include a variety of conventional or non-conventional structures. In some cases, the configuration of sole member 1700 can be selected or customized according to one or more types of ground surfaces on which sole member 1700 may be used. Examples of ground surfaces include, but are not limited to, natural turf, synthetic turf, dirt, as well as other surfaces.

Upon obtaining measurements of foot 1500 (see FIG. 15), sole member 1700 may be adjusted or altered in different embodiments. As seen in the virtual representation depicted in FIG. 18, using the data collected from the steps above, a first custom sole 1800 may be designed. In some embodiments, the design may utilize an application of an integrated computer-aided design such as a computer-automated manufacturing (CAD-CAM) process. Sole member 1700, or any other template previously selected, may be provided as an input to the computer design program. In one embodiment, the three-dimensional foot shape data from virtual scan 1600 in FIG. 16 is also provided to the program.

In different embodiments, virtual scan 1600 may provide information regarding foot shape and pressure to allow appropriate fit and comfort within the article of footwear. The information may be used to form first custom sole 1800. In some embodiments, data from virtual scan 1600 may be superimposed or otherwise incorporated into the template of sole member 1700 (see FIGS. 16 and 17). For example, there may be a process of aligning the data representing the plantar pressures of foot 1500 with sole member 1700 and generating a partial or complete design of first custom sole 1800. In one embodiment, pressure contour lines 1806 may be generated during the design of first custom sole 1800. The pressure distribution may be adjusted to a "best-fit" position based upon user input in some embodiments. Once the distribution is finalized, a resiliency profile may be created. For purposes of this disclosure, a resiliency profile is a personalized pressure distribution for a user that may include the data collected during the steps described above. In some embodiments, the resiliency profile may be utilized in the production of first custom sole 1800. Thus, in one embodiment, after the resiliency profile comprising an individual's plantar pressure distributions is aligned with the template of sole member 1700, a customized sole member may be formed or manufactured.

It should be understood that, in different embodiments, the design of a sole member may include various modifications. Customized modifications may provide individual users with a wider range of comfort and fit. For example, different users may have differences in the height of the arch of foot 1500. As described above, foot 1500 may include multiple arches. Generally, the arch is a raised curve on the bottom surface of foot 1500. When the tendons of foot 1500 pull a normal amount, foot 1500 generally forms a moderate or normal arch. However, when tendons do not pull together properly, there may be little or no arch. This is called "flat foot" or fallen arch. Over-pronation of a foot may be common for those with flat feet. The framework of a foot can collapse, causing the foot to flatten and adding stress to other parts of the foot. Individuals with flat feet may need orthotics to control the flattening of the foot. Moreover, the opposite may also occur, though high foot arches are less common than flat feet. Without adequate support, highly arched feet tend to be painful because more stress is placed on the section of the foot between the ankle and toes. This condition can make it difficult to fit into shoes. Individuals who have high arches usually need foot support. It should be noted that such variations in arch height are one of many possible examples of customized foot geometry that may be incorporated into a design.

Figure 19:
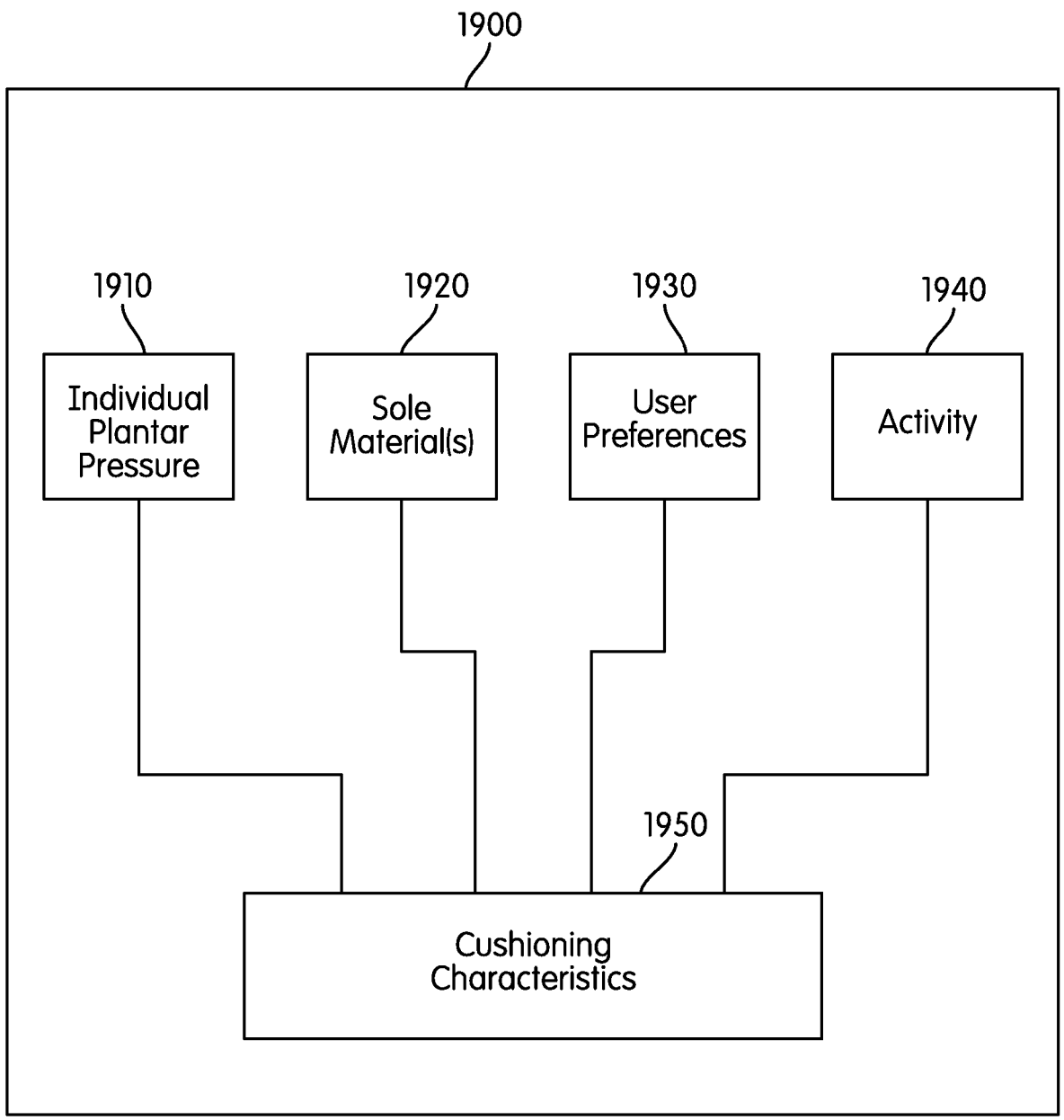
FIG. 19 is an embodiment of an influence diagram.

Referring to FIG. 19, an embodiment of an influence diagram 1900 is depicted. Influence diagram 1900 reflects some of the factors or variables that can be considered, incorporated, and/or used during the generation of the resiliency profile, permitting customization of cushioning characteristics 1950 of a sole member. For example, a first factor 1910 includes an individual's measured plantar pressure for each foot, which was discussed above with respect to FIG. 15-16. In addition, a second factor 1920 may include the materials that will be used to form the custom sole member. A third factor 1930 can be the individual user's own personal preferences regarding the type or level of cushioning desired. A fourth factor 1940 may be the activity or sport that the user will be generally engaging in while using the custom sole member. In some cases, the sole member can be designed or tailored to provide special cushioning in areas or regions of the sole member that typically experience more force or pressure from the foot during specific activities. Thus, in some embodiments, one or more of these factors can contribute to cushioning characteristics 1950 of a sole member. It should be understood that influence diagram 1900 is provided as an example, and many other factors not listed here may be included in other embodiments. Furthermore, one or more factors listed in influence diagram 1900 may be removed from consideration depending on the desired output or the goal of the custom sole member.

Once a design has been generated, as with first custom sole 1800, the sole member may be manufactured. In some embodiments, the modifications may include regions of the sole member with apertures 150 disposed along different portions of the sole member. In some embodiments, a sole member can be molded in a manner that creates apertures in the sole member. An article of footwear including apertures can be formed in any manner. In some embodiments, apertures can be created in a sole member using any known methods of cutting or drilling. For example, in one embodiment, apertures can be created using laser cutting techniques. Specifically, in some cases, a laser can be used to remove material from a sole member in a manner that forms apertures in the sole member. In another embodiment, a hot knife process could be used for forming apertures in a sole member. Examples of methods for forming apertures on a sole member are disclosed in McDonald, U.S. Pat. No. 7,607,241, issued Oct. 27, 2009, titled "Article of Footwear with an Articulated Sole Structure," (previously U.S. patent application Ser. No. 11/869,604, filed Oct. 9, 2007), the entirety of which is hereby incorporated by reference. In other embodiments, however, any other type of cutting method can be used for forming apertures. Furthermore, in some cases, two or more different techniques can be used for forming apertures. As an example, in another embodiment, apertures disposed on a side surface of a sole member can be formed using laser cutting, while apertures on a lower surface of the sole member could be formed during a molding process. Still further, different types of techniques could be used according to the material used for a sole member. For example, laser cutting may be used in cases where the sole member is made of a foam material.

Figure 20:
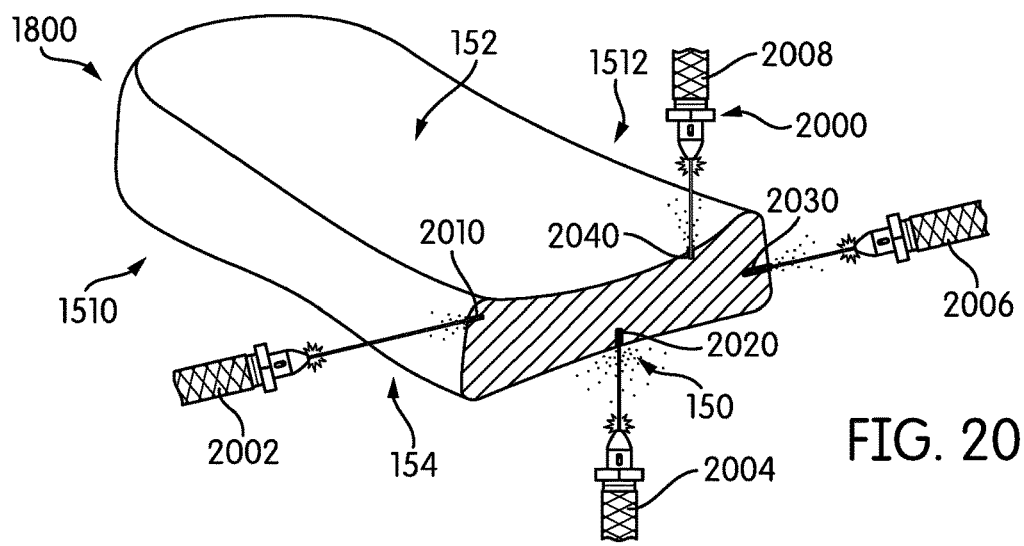
FIG. 20 is a schematic cutaway view of an embodiment of a sole member during a process of forming apertures.
Figure 21:
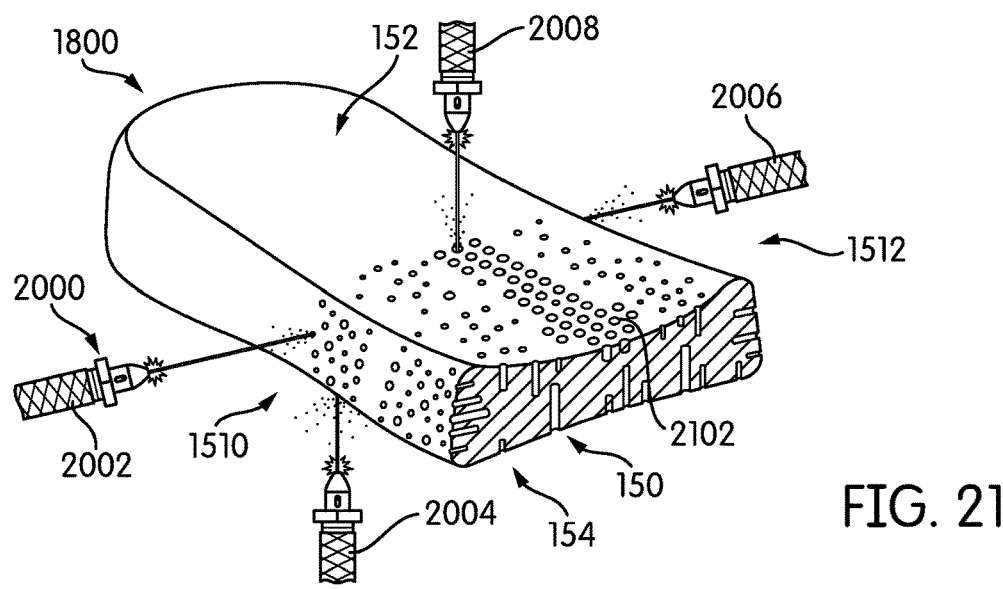
FIG. 21 is a schematic cutaway view of an embodiment of a sole member during a process of forming apertures.
Figure 22:
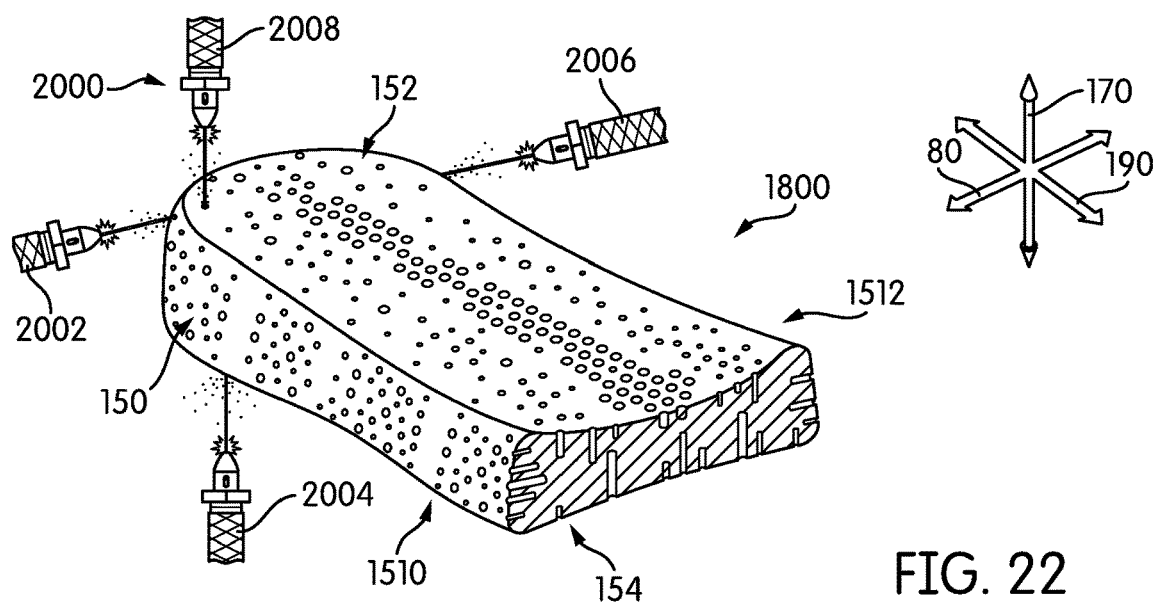
FIG. 22 is a schematic cutaway view of an embodiment of a sole member during a process of forming apertures.

In FIGS. 20-22, a sequence of figures depicting the formation of first custom sole 1800, including apertures, is shown. Referring to FIG. 20, one or more apertures can be applied to or formed in first custom sole 1800 using laser drills 2000. In this case, laser drills 2000 include a first laser 2002, a second laser 2004, a third laser 2006, and a fourth laser 2008. In other cases, there may be a fewer or greater number of lasers. In FIG. 20, laser drills 2000 have begun to engage the material of first custom sole 1800, and a few apertures are being formed along each surface of first custom sole 1800. In FIG. 20, first laser 2002 is forming a first aperture 2010, second laser 2004 is forming a second aperture 2020, third laser 2006 is forming a third aperture 2030, and fourth laser 2008 is forming a fourth aperture 2040. Each aperture can be associated with an opening 2102 along the outer surface. Although only apertures in one general region are shown in this example, it will be understood that a similar method could be used for creating apertures in any other region of first custom sole 1800. It should further be understood that laser drills 2000 may include provisions for moving along different directions in order to direct the laser beam to the desired location. Furthermore, the sole member may be disposed such that it may be automatically or manually moved to receive the laser beam at the appropriate location. In addition, while all four laser drills 2000 are shown in use in FIGS. 20-22, in other embodiments, only one, two, or three lasers may be engaged with the material.

Thus, referring to FIGS. 20-22, multiple lasers can be used to simultaneously form two or more different apertures along different areas of first custom sole 1800. During a first step, illustrated in FIG. 20, first laser 2002 may be associated with lateral side 1510, second laser 2004 may be associated with lower surface 154, third laser 2006 may be associated with medial side 1512, and fourth laser 2008 may be associated with upper surface 152. Following this, during a second step that is illustrated in FIG. 21, one or more of first laser 2002, second laser 2004, third laser 2006, and fourth laser 2008 may move so that one or more laser beams may cut through a different portion or region of the material of first custom sole 1800. Finally, during a third step that is illustrated in FIG. 22, first laser 2002, second laser 2004, third laser 2006, and fourth laser 2008 may remove material from the rearmost portion of first custom sole 1800, forming apertures 150 throughout the desired portions of first custom sole 1800. It may be recalled that apertures may be formed such that they differ in one or more respects from one another, or they may be formed in a uniform manner, such that they are substantially similar in size, length, and shape. Furthermore, it should be understood that laser drills 2000 may be oriented at an angle different from those shown in FIGS. 20-22, such that laser drills 2000 can form apertures 150 oriented in a diagonal or non-parallel manner with respect to vertical axis 170, longitudinal axis 180, and/or lateral axis 190.

Thus, as described herein, in some embodiments, the arrangement of apertures on a sole member could be varied to tune properties of the sole member for specific types of physical or personal characteristics, and/or athletic activities. For example, in some cases, the arrangement of apertures on a sole member could be selected according to the type of sport for which the article of footwear is intended. In some embodiments, a manufacturer could vary the arrangement of apertures for various types of footwear, including, but not limited to, soccer footwear, running footwear, cross-training footwear, basketball footwear, as well as other types of footwear. Additionally, in other embodiments, the arrangement of apertures on a sole member could be varied according to the gender of the intended user. For example, in some cases, the aperture arrangements may vary between footwear for men and footwear for women. Still further, in some embodiments, the arrangement of apertures on a sole member could be varied according to preferences of a user for achieving desired performance effects. As an example, a desire for increased flexibility on a lateral side of the article can be accommodated by increasing the number and/or size of apertures on the lateral side of the sole member. In addition, in some embodiments, the configuration of apertures on a sole could be varied to achieve various visual or graphical effects. Furthermore, as discussed above, the arrangement of apertures can be individually customized by measuring various pressure regions of a person's foot and applying that information to the positioning and type of apertures on the sole member.

It should be understood that methods of customizing aperture configuration for particular sports, gender, and/or personal preferences can be achieved in any manner. In one embodiment, a method of customizing aperture configuration for an article can include provisions for allowing a user to select a customized aperture arrangement by interacting with a website that provides customization tools for varying the number and/or geometry of various apertures. Examples of different customization systems that can be used for customizing aperture configurations are disclosed in Allen et al., U.S. Patent Publication Number 2005/0071242, published Mar. 31, 2005, titled "Method and System for Custom-Manufacturing Footwear," (previously U.S. patent application Ser. No. 10/675,237, filed Sep. 30, 2003), and Potter et al., U.S. Patent Publication Number 2004/0024645, published Feb. 5, 2004, titled "Custom Fit Sale of Footwear," (previously U.S. patent application Ser. No. 10/099,685, filed Mar. 14, 2002) the entirety of both being hereby disclosed by reference. It will be understood that the method of customizing aperture arrangements for an article of footwear are not limited to use with any particular customization system, and in general, any type of customization system known in the art could be used.

Articles of the embodiments discussed above may be made from materials known in the art for making articles of footwear. For example, a sole member may be made from any suitable material, including, but not limited to, elastomers, siloxanes, natural rubber, other synthetic rubbers, aluminum, steel, natural leather, synthetic leather, foams, or plastics. In an exemplary embodiment, materials for a sole member can be selected to enhance the overall flexibility, fit, and stability of the article. In one embodiment, a foam material can be used with a sole member, as foam can provide the desired elasticity and strength. In another embodiment, a rubber material could be used to make a midsole of a sole member. In still another embodiment, a thermoplastic material could be used with a sole member. For example, in one embodiment, thermoplastic polyurethane (TPU) may be used to make a midsole for a sole member. In still other embodiments, a sole member may comprise a multi-density insert that comprises at least two regions of differing densities. For example, in one other embodiment, a midsole of a sole member could be configured to receive one or more inserts. Examples of different types of inserts that could be used are disclosed in Yu et al., U.S. Pat. No. 7,941,938, issued May 17, 2011, titled "Article of Footwear with Lightweight Sole Assembly," (previously U.S. patent application Ser. No. 11/752,348, filed Mar. 23, 2007) the entirety of which is hereby incorporated by reference. Also, an upper may be made from any suitable material known in the art, including, but not limited to, nylon, natural leather, synthetic leather, natural rubber, or synthetic rubber.

An article of footwear can include provisions for adjusting the flexibility characteristics of a sole member with a plurality of apertures. In some embodiments, different materials can be used with different portions of a sole. In an exemplary embodiment, portions of a sole can be filled with additional material or components to provide different types of cushioning, feel, and flexibility for a sole member. For example, in one embodiment, a core portion of a sole member may comprise a fluid-filled member, such as an air bladder. In another embodiment, one or more portions of a sole member could include hollow cavities capable of receiving fluid or other materials.

Figure 23:
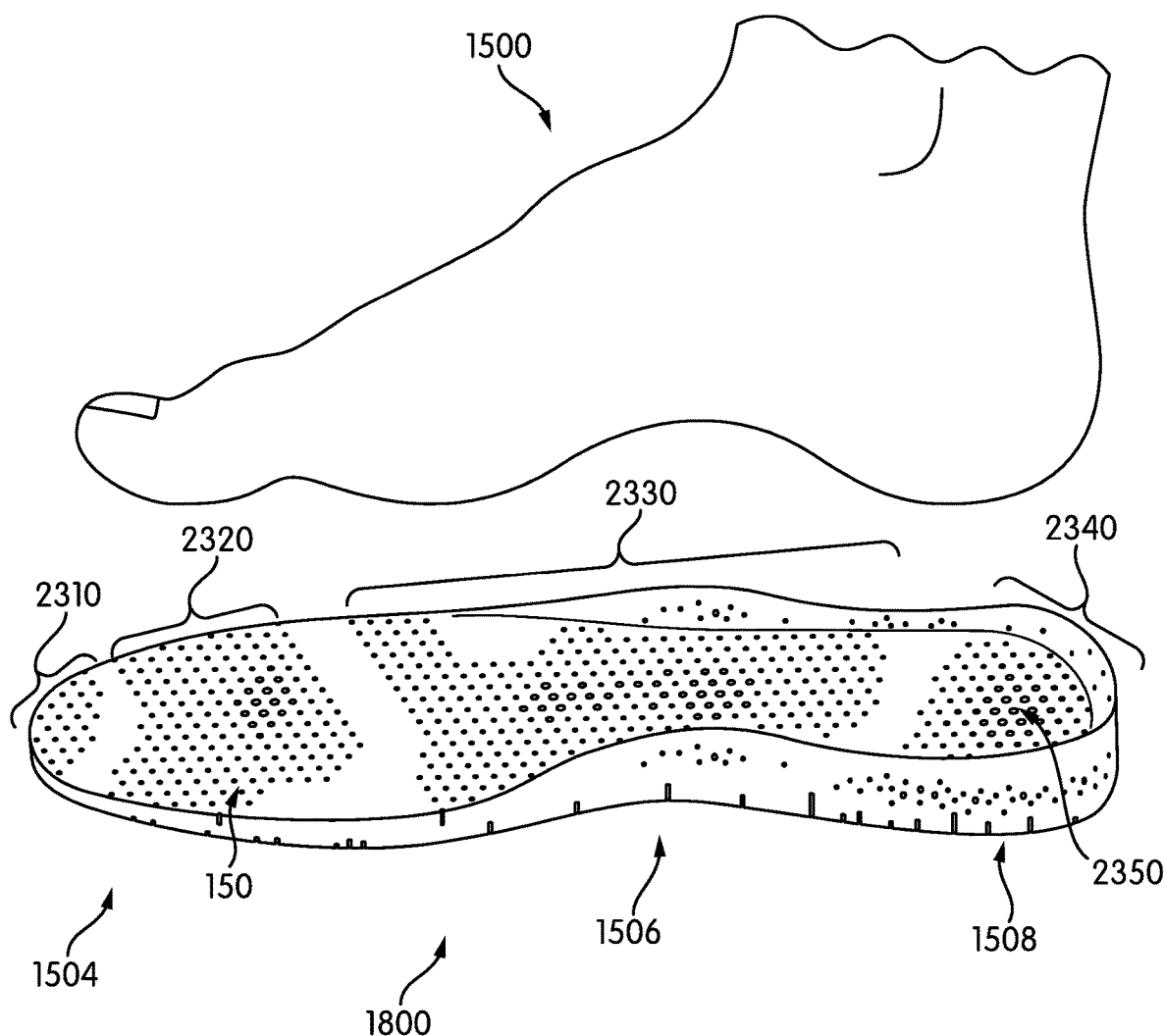
FIG. 23 is an isometric side view of an embodiment of a sole member.

In FIG. 23, an embodiment of the completed first custom sole 1800 is shown with foot 1500. As shown in FIG. 23, first custom sole 1800 includes apertures 150 in regions that generally correspond to the regions of foot 1500 that were indicated to have increased plantar pressures (see FIGS. 15 and 16). In other words, the plantar pressure distribution comprising pressure contour lines 1806 (see FIG. 18) is generally aligned with the disposition of apertures 150 in first custom sole 1800. Thus, in one embodiment, first pressure area 1604, second pressure area 1606, third pressure area 1608, fourth pressure area 1610, and/or fifth pressure area 1612 (see FIG. 16) can be accommodated by or correspond to different sets of apertures 150 formed in first custom sole 1800.

In FIG. 23, a first set of apertures 2310, a second set of apertures 2320, a third set of apertures 2330, and a fourth set of apertures 2340 are shown. Referring to FIG. 16, first pressure area 1604 is associated with the toes of foot 1500. As a result, in FIG. 23, first set of apertures 2310 are disposed near the foremost area of forefoot region 1504. In addition, second pressure area 1606 and third pressure area 1608 are associated with the inner and outer ball of foot 1500 in forefoot region 1504 (see FIG. 16). Thus, second set of apertures 2320 have been formed along forefoot region 1504 of first custom sole 1800 in FIG. 23. Additionally, fourth pressure area 1610 in FIG. 16 is associated with the longitudinal arch of foot 1500, and so third set of apertures 2330 in FIG. 23 have been formed through midfoot region 1506 of first custom sole 1800. Finally, as fifth pressure area 1612 is associated with heel region 1508 of foot 1500 (see FIG. 16), fourth set of apertures 2340 have been disposed along heel region 1508 of first custom sole 1800 in FIG. 23. Although not illustrated here, it should be understood that other areas of foot 1500 may also be cushioned in different ways.

Depending on the magnitude of the measured plantar pressures, apertures in each area can be larger or more numerous. In other words, in areas of the foot associated with higher plantar pressures, the number and/or size of apertures may be increased. For example, in some embodiments, the plantar pressure associated with heel region 1508 may be largest. In such embodiments, there can be one or more larger apertures 2350 disposed in heel region 1508 relative to other regions of first custom sole 1800, as shown in FIG. 23.

Thus, in some embodiments, custom sole members as described herein can cushion the plantar pressures associated with forefoot region 1504, midfoot region 1506, and/or heel region 1508, and may help offload areas of higher pressures. A more appropriate type and amount of cushioning can be generated for a user using the embodiments of a customized cushioning sole system depicted herein, reducing the amount of pressure experienced by foot 1500. For example, if plantar pressure values are determined to be atypical, the information can be used to modify a person's footwear (e.g., the sole member) to provide the person with footwear more effective in producing a more typical pattern of foot loading during walking or other activities.

Figure 24:
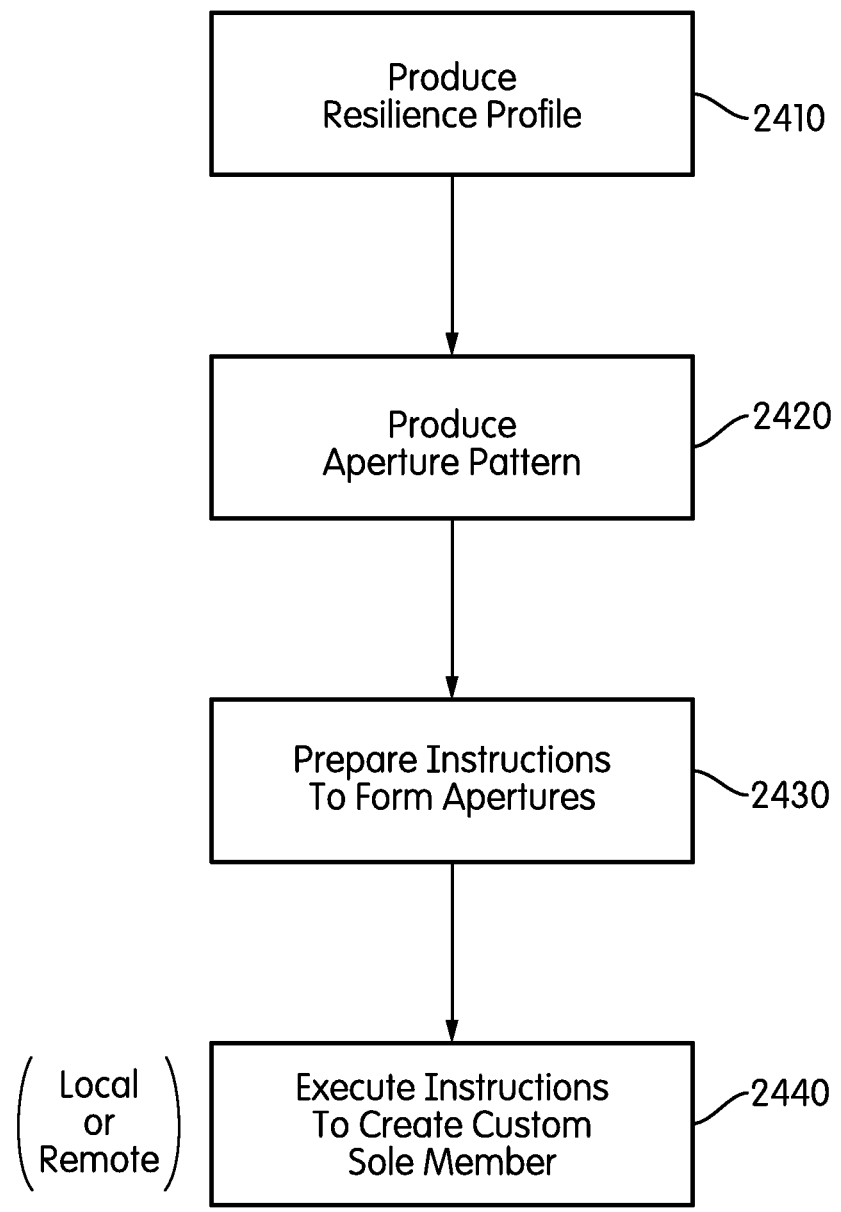
FIG. 24 is an embodiment of a flow chart for a method of making a custom sole member.

An embodiment of the sole member production process as described herein is outlined in the flow chart of FIG. 24. In a first step 2410, a pressure distribution of a user's feet is obtained (see FIGS. 15-18 above). The pressure distribution as well as any other preferences are collected to generate a resiliency profile. In a second step 2420, the resiliency profile may be used to produce a custom configuration or pattern of apertures (e.g., position, size, lengths, orientation, etc.) in a sole member. The particular configuration of apertures generated may be stored in a virtual or digital form in some embodiments. Following the production of an aperture pattern, instructions to form the apertures in a sole member may be prepared or generated in a third step 2430. In some cases, the aperture pattern may be converted into a series of commands or instructions for a system to follow in order to translate the aperture pattern into mechanical or design steps for forming the customized sole member. Finally, in a fourth step 2440, the instructions are executed and a custom sole member is produced.

The process described herein may occur in rapid succession and in close proximity to one another in some embodiments. However, in other embodiments, one or more steps may occur spaced apart in time and location. In other words, one step may occur in a first location, and another step may occur in a second location, where the first location is different from the second location. For example, the resiliency profile of first step 2410 may be produced off-site (e.g., at a shopping outlet or a medial office, etc.), and the aperture pattern of second step 2420 may be produced in a manufacturing facility. In another example, the instructions for forming the apertures of third step 2430 may be prepared or generated in a local site, while the actual production of the custom sole member of fourth step 2440 may occur in a remote site (e.g., out of state, or abroad).

Figure 25:
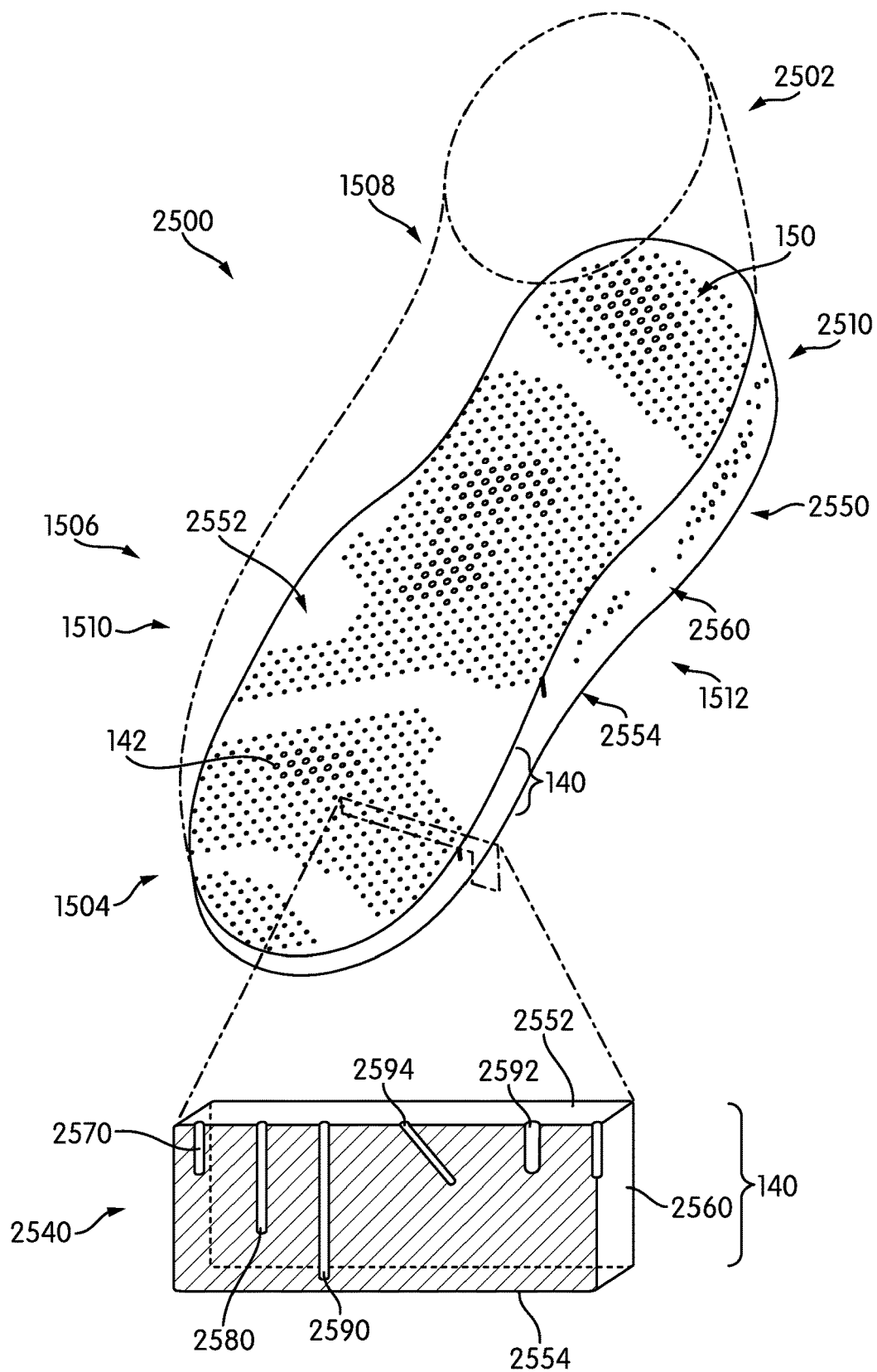
FIG. 25 is an isometric top view of an embodiment of a sole member.
Figure 26:
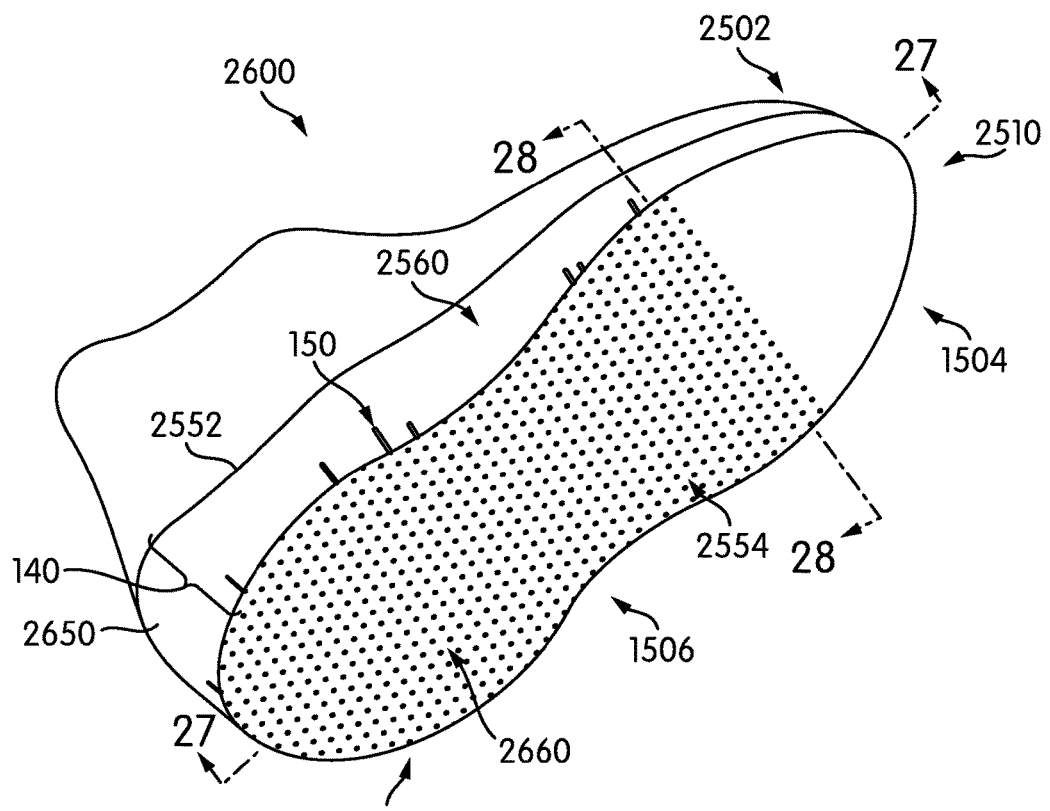
FIG. 26 is an isometric bottom view of an embodiment of a sole member.

FIGS. 25 and 26 illustrate alternative embodiments of a custom sole member for an article of footwear. Referring to FIG. 25, a first article of footwear ("first article") 2500 is shown, and in FIG. 26, a second article of footwear ("second article") 2600 is shown. First article 2500 and second article 2600 can be configured as any type of footwear including, but not limited to, hiking boots, soccer shoes, football shoes, sneakers, rugby shoes, basketball shoes, baseball shoes as well as other kinds of footwear. Each article of footwear can comprise an upper 2502 and a sole structure 2510. Sole structure 2510 is secured to upper 2502 and extends between the foot and the ground when the article is worn. In different embodiments, sole structure 2510 may include different components. For example, sole structure 2510 may include an outsole, a midsole, and/or an insole. In some cases, one or more of these components may be optional. In one embodiment, sole structure 2510 may include a sole member, as described above.

Generally, a customized sole member may comprise any layer or element of sole structure 2510, and be configured as desired. In particular, layers or portions of the sole member may have any design, shape, size, and/or color. For example, in embodiments where an article of footwear is a basketball shoe, a sole member could include contours shaped to provide greater support to heel prominence. In embodiments where the article of footwear is a running shoe, the custom sole member could be configured with contours supporting forefoot region 1504. In some embodiments, sole structure 2510 could further include provisions for fastening to an upper or another sole layer, and may include still other provisions found in footwear sole members. Also, some embodiments of sole structure 2510 may include other materials disposed within the custom sole member, such as air bladders, leather, synthetic materials (such as plastic or synthetic leather), mesh, foam, or a combination thereon.

The material selected for sole structure 2510 and/or a sole member may possess sufficient durability to withstand the repetitive compressive and bending forces that are generated during running or other athletic activities. In some embodiments, the material(s) may include foams; polymers such as urethane or nylon; resins; metals such as aluminum, titanium, stainless steel, or lightweight alloys; or composite materials that combine carbon or glass fibers with a polymer material, ABS plastics, PLA, glass-filled polyamides, stereolithography materials (epoxy resins), silver, titanium, steel, wax, photopolymers, and polycarbonate. The customized sole member may also be formed from a single material or a combination of different materials. For example, one side of a custom sole member may be formed from a polymer whereas the opposing side may be formed from a foam. In addition, specific regions may be formed from different materials depending upon the anticipated forces experienced by each region.

In FIG. 25, an isometric top view of upper 2502 (shown in dotted line) with sole structure 2510 is shown, where sole structure 2510 includes a second custom sole 2550. For purposes of reference, an upper surface 2552 is identified on the upper side of second custom sole 2550, and a lower surface 2554 is identified on the bottom side. Extending along the perimeter and thickness, between upper surface 2552 and lower surface 2554, is a sidewall 2560. Together, upper surface 2552, lower surface 2554, and sidewall 2560 comprise an exterior surface of second custom sole 2550. Disposed along various portions of the exterior surface are apertures 150 that extend varying lengths through thickness 140 of second custom sole 2550.

As discussed above, in some embodiments, apertures 150 may be disposed on all surfaces of second custom sole 2550. In other embodiments, apertures 150 may be disposed on only one or two surfaces of second custom sole 2550. In FIG. 25, apertures 150 are formed along upper surface 2552. Openings 142 are visible near the perimeter of heel region 1508, along midfoot region 1506, and in portions of forefoot region 1504. Furthermore, additional openings 142 are disposed along medial side 1512 of sidewall 2560.

A cutaway section 2540 is included in FIG. 25, providing a view of a portion of the interior of second custom sole 2550. In cutaway section 2540, six openings 142 corresponding to six apertures are shown formed through upper surface 2552. As discussed above, apertures may extend different lengths through second custom sole 2550. In FIG. 25, a first aperture 2570, a second aperture 2580, and a third aperture 2590 are illustrated. It can be seen that first aperture 2570 has a length that is less than the length of second aperture 2580, and second aperture 2580 has a length that is less than the length of third aperture 2590. In different embodiments, the lengths of first aperture 2570, second aperture 2580, and third aperture 2590 may be similar or may differ, as described with reference to FIGS. 1-5. For example, in other embodiments, first aperture 2570 may be shorter (smaller in length) than second aperture 2580 and/or third aperture 2590.

Furthermore, apertures may comprise varying sizes. The overall cross-sectional size of first aperture 2570 is smaller than that of a fourth aperture 2492. In different embodiments, the size of each aperture may be similar or may differ from that depicted here. For example, in other embodiments, first aperture 2570 may be larger than fourth aperture 2592. Thus, in some embodiments, apertures 150 disposed on second custom sole 2550 can have varying sizes with respect to one another, or they may have the same size. In other embodiments, apertures 150 disposed on one surface (e.g., sidewall 2560) may be larger than apertures 150 disposed on another surface (e.g., upper surface 2552). Furthermore, apertures 150 may vary with respect to one another in shape along each surface, or the shapes may each be the same. In other embodiments, apertures 150 may differ from one another in both size and shape along the same surface.

Furthermore, as noted earlier, the orientation of an aperture may differ from neighboring apertures. In FIG. 25, a fifth aperture 2594 is depicted. Fifth aperture 2494 is disposed at a substantially diagonal angle relative to third aperture 2590 and fourth aperture 2592. Thus, in some embodiments, depending on the cushioning characteristics desired, the orientation or alignment properties of apertures 150 may be customized or altered.

In FIG. 26, a bottom isometric view of an embodiment of second article 2600 is illustrated, including upper 2502 and sole structure 2510, where sole structure 2510 includes a third custom sole 2650. Third custom sole 2650 includes a set of apertures 2660 disposed over substantially the entire length and width of lower surface 2554 from midfoot region 1506 to heel region 1508. In some embodiments, there may also be apertures 150 disposed on sidewall 2560 of third custom sole 2650.

Figure 27:
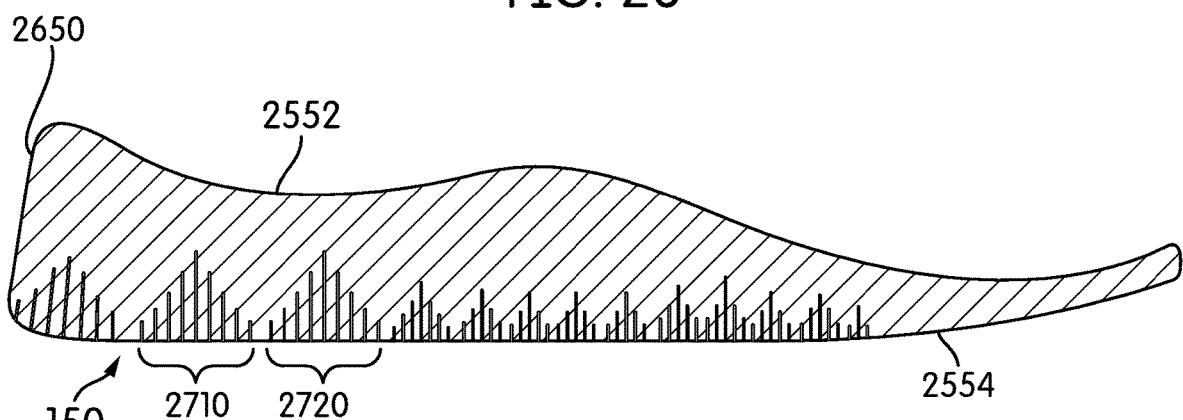
FIG. 27 is a longitudinal cross section of an embodiment of the sole member of FIG. 26.

Furthermore, as seen in FIG. 27, where a longitudinal cross section of third custom sole 2650 along the line 27-27 is represented, at least some of the apertures in set of apertures 2660 are arranged in a generally oscillating pattern. Specifically, referring to a first pattern 2710 of apertures, the respective lengths of the apertures gradually increase and then decrease or taper toward zero before beginning another series of apertures (e.g., a second pattern 2720). As noted above, apertures 150 may be arranged in a geometric pattern to provide a wearer with enhanced or improved support and cushioning, and such an oscillating pattern may improve the comfort and feel of the sole member for a foot.

Figure 28:
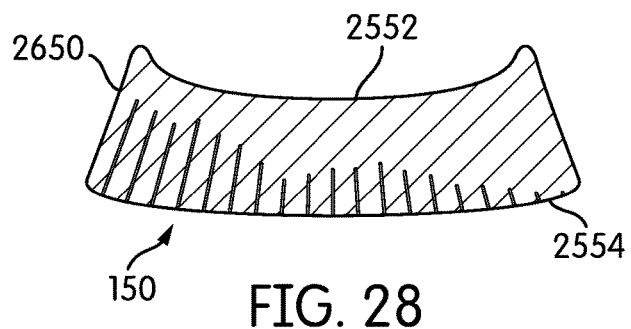
FIG. 28 is a lateral cross section of an embodiment of the sole member of FIG. 26.

In addition, as seen in FIG. 28, where a lateral cross section of third custom sole 2650 along the line 28-28 is represented, at least some of the apertures in set of apertures 2660 are arranged in an irregular fashion. In other words, in some cases, the lengths of apertures may not follow a geometric pattern. As noted above, apertures may be configured to perform specialized or customized support and cushioning. Thus, in different embodiments, as shown in FIGS. 27 and 28, third custom sole 2650 can provide both generalized cushioning, as well as specialized (i.e., uniquely tailored) cushioning.

Thus, the various cushioning elements as described here can provide a custom sole member with specialized responses to ground reaction forces. In one embodiment, the cushioning element may attenuate and distribute ground reaction forces. For example, when a portion of the custom sole member contacts the ground, the apertures disposed in cushioning element can help attenuate the ground reaction forces. The cushioning element may have the capacity to distribute the ground reaction forces throughout a substantial portion of the custom sole member. The attenuating property of this type of structure can reduce the degree of the effect that ground reaction forces have on the foot, and the distributive property can spread the ground reaction forces to various portions of a foot. In some embodiments, such features may reduce the peak ground reaction force experienced by the foot.

In other embodiments, the cushioning element designs disclosed in this description may also include provisions to achieve a non-uniform ground reaction force distribution. For example, the ground reaction force distribution of a custom sole member could provide a wearer with a response similar to that of barefoot running, but with attenuated ground reaction forces. That is, the custom sole member could be designed to impart the feeling of barefoot running, but with a reduced level of ground reaction forces. Additionally, in another example, the ground reaction forces could be more concentrated in the medial side of a foot than along the lateral side of a foot, thereby reducing the probability that the foot will over-pronate, or imparting greater resistance to eversion and inversion of the foot.

In some embodiments, the use of cushioning elements in orthotics for an article of footwear can help support weakened areas of a foot and assist the user in each step. While a relatively rigid material, as may be included in a custom sole member, can provide functional support to the foot, softer or more flexible regions associated with apertures can absorb the loads put on the foot and provide protection. Such softer or cushioned regions can better absorb the loads placed on a foot, increase stabilization, and take pressure off uncomfortable or sore spots of the feet.

Other embodiments or variations of custom sole members may include other aperture patterns or various combinations of the above-disclosed designs. It should be noted that the present description is not limited to cushioning elements having the geometry or aperture configurations of first custom sole 1800, second custom sole 2550, and third custom sole 2650. In different embodiments, each customized sole member may include further variations not depicted in the figures. Some variations may include differences in shape, size, contour, elevations, depressions, curvatures, and other variations of the sole member. In other words, the custom sole members depicted herein are merely intended to provide an example of the many types of cushioning element-based sole member configurations that fall within the scope of the present discussion.

In different embodiments, sole members as well as any apertures in the sole members discussed herein may be formed using any other method known in the art. In some embodiments, any removal process (i.e., where a portion of a material is removed, subtracted, eliminated, etc.) may be used to form one or more apertures (e.g., apertures 150). For example, in some embodiments, a mechanical process may be used, including but not limited to ultrasonic machining, water jet machining, abrasive jet machining, abrasive water jet machining, ice jet machining, and/or magnetic abrasive finishing. In other embodiments, chemical processes may be utilized, including but not limited to chemical milling, photochemical milling, and/or eletropolishing. Furthermore, in some embodiments, electrochemical processes may be used. In other embodiments, thermal processes can be used, such as electrodischarge machining (EDM), laser beam machining, electron beam machining, plasma beam machining, and/or ion beam machining, or other processes. In another embodiment, hybrid electrochemical processes can be utilized, including but not limited to electrochemical grinding, electrochemical honing, electrochemical superfinishing, and/or electrochemical buffing. In addition, hybrid thermal processes may be used, such as electroerosion dissolution machining. In other embodiments, the material comprising the sole member may be modified using chemical processes, including temperature changes (e.g., freezing the material). Furthermore, the processes for forming the apertures may be applied or utilized after the article of footwear has been assembled, or the sole member has been associated with an upper or sole structure. In other words, the formation of apertures in a sole member may occur post-manufacturing of the article of footwear.

It should be understood that in other embodiments, the midsole can include a casing in a molded foam. In other words, embodiments of the sole member as described herein may be associated with the midsole of a sole structure. Thus, in some embodiments, a midsole may include a foam material. The foam material can comprise a 'skin' surface that is formed from a molding process. In some embodiments, the various removal processes described above (e.g., drilling, laser, chemical, EDM, water cutting, etc.) can be applied to the foam skin of a midsole and apertures can be formed in a manner similar to the embodiments discussed above.

While various embodiments have been described, the description is intended to be exemplary, rather than limiting, and it will be apparent to those of ordinary skill in the art that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with or substituted for any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

What is claimed is:

1. A method for making a customized sole member for an article of footwear, comprising:
    obtaining information related to a wearer's foot including at least: (a) three-dimensional information corresponding to size and geometry of the wearer's foot and (b) information regarding plantar pressure applied to a surface by the wearer's foot;
    producing a pattern of apertures to be cut into a polymer foam sole member by a laser, wherein the pattern of apertures is produced based on the information relating to the wearer's foot and includes an arrangement of apertures to be formed in the polymer foam sole member at locations with respect to the wearer's foot to provide a desired set of cushioning characteristics, wherein the pattern of apertures includes: (a) a first set of apertures extending from a top surface or a bottom surface of the polymer foam sole member and into an interior of the polymer foam sole member and (b) a sidewall set of apertures including a plurality of blind-hole apertures extending from a sidewall surface of the polymer foam sole member and into the interior of the polymer foam sole member;

generating instructions to form the pattern of apertures in the polymer foam sole member; and executing the instructions to form the polymer foam sole member to include the pattern of apertures and thereby produce the customized sole member for the wearer's foot, wherein the step of executing the instructions includes laser cutting the pattern of apertures in the polymer foam sole member.

2. The method of claim 1, further comprising obtaining information about preferences of the wearer related to cushioning of the article of footwear, and wherein the pattern of apertures is determined based in part on the information obtained about the preferences.

3. The method of claim 1, wherein each aperture in the pattern of apertures has a length, and wherein each length is determined based on the information obtained related to the wearer's foot.

4. The method of claim 1, wherein a first plurality of apertures of the sidewall set of apertures extend along a lateral axis of the polymer foam sole member and a second plurality of apertures of the sidewall set of apertures extend along a longitudinal axis of the polymer foam sole member.

5. The method of claim 1, wherein the first set of apertures includes apertures extending from the bottom surface of the polymer foam sole member and into the interior of the polymer foam sole member, and wherein the pattern of apertures further includes a top surface set of apertures extending from the top surface of the polymer foam sole member into the interior of the polymer foam sole member.

6. The method of claim 1, wherein the step of producing the pattern of apertures includes determining position, size, length, number, and orientation of apertures in the pattern of apertures to be cut in the polymer foam sole member to produce the desired set of cushioning characteristics.

7. A method for making a customized sole member for an article of footwear, comprising:
obtaining information relating to a user's foot including at least: (a) three-dimensional information corresponding to size and geometry of the user's foot and (b) information regarding plantar pressure applied to a surface by the user's foot;

producing a pattern of apertures to be cut into a foam material of a sole member by a laser based on the information obtained relating to the user's foot, wherein the pattern of apertures produced includes an arrangement of apertures to be formed in the sole member made from the foam material at locations with respect to the user's foot to provide a desired set of cushioning characteristics, wherein the pattern of apertures includes: (a) a first set of apertures having between 40 and 70 blind-hole apertures extending from a lower surface of the sole member and terminating in an interior of the sole member and (b) a sidewall set of apertures including a plurality of blind-hole apertures extending from a sidewall surface of the sole member and into the interior of the sole member;

generating instructions to form the pattern of apertures in the foam material of the sole member; and executing the instructions to form the foam material of the sole member to include the pattern of apertures and thereby produce the customized sole member for the user's foot, wherein the step of executing the instructions includes laser cutting the pattern of apertures in the foam material of the sole member.

8. The method of claim 7, wherein the pattern of apertures further includes a second set of apertures having more than 100 blind-hole apertures extending from an upper surface of the sole member into and terminating in the interior of the sole member.

9. The method of claim 7, wherein a first plurality of apertures of the sidewall set of apertures extend along a lateral axis of the sole member and a second plurality of apertures of the sidewall set of apertures extend along a longitudinal axis of the sole member.

10. The method of claim 7, wherein the step of producing the pattern of apertures includes determining position, size, length, number, and orientation of apertures in the pattern of apertures to be cut in the foam material to produce the desired set of cushioning characteristics.

11. A method for making a customized sole member for an article of footwear, comprising:
obtaining information relating to a user's foot including at least: (a) three-dimensional information corresponding to size and geometry of the user's foot and (b) information regarding plantar pressure applied to a surface by the user's foot;

producing a pattern of apertures to be cut into a foam material of a sole member by a laser based on the information obtained relating to the user's foot, wherein the pattern of apertures produced includes an arrangement of apertures to be formed in the sole member made from the foam material at locations with respect to the user's foot to provide a desired set of cushioning characteristics, wherein the pattern of apertures includes: (a) a first set of apertures having more than 100 blind-hole apertures extending from one of an upper surface or a lower surface of the sole member and terminating in an interior of the sole member and (b) a sidewall set of apertures including a plurality of blind-hole apertures extending from a sidewall surface of the sole member and into the interior of the sole member;

generating instructions to form the pattern of apertures in the foam material of the sole member; and executing the instructions to form the foam material of the sole member to include the pattern of apertures and thereby produce the customized sole member for the user's foot, wherein the step of executing the instructions includes laser cutting the pattern of apertures in the foam material of the sole member.

12. The method of claim 11, wherein the first set of apertures extend from the lower surface into the interior of the sole member.

13. The method of claim 11, wherein the first set of apertures extend from the upper surface into the interior of the sole member.

14. The method of claim 11, wherein the first set of apertures extend from the upper surface into the interior of the sole member, and wherein the pattern of apertures further includes a second set of apertures having from 40 to 70 apertures extending from the lower surface of the sole member into the interior of the sole member.

15. The method of claim 11, wherein the first set of apertures extend from the lower surface into the interior of the sole member, and wherein the pattern of apertures further includes a second set of apertures extending from the upper surface of the sole member into and terminating in the interior of the sole member.

16. The method of claim 15, wherein the second set of apertures includes more than 100 apertures.

17. The method of claim 15, wherein the second set of apertures includes between 1 and 30 apertures.

18. The method of claim 15, wherein the second set of apertures includes more than 30 apertures.

19. The method of claim 11, wherein a first plurality of apertures of the sidewall set of apertures extend along a lateral axis of the sole member and a second plurality of apertures of the sidewall set of apertures extend along a longitudinal axis of the sole member.

20. The method of claim 11, wherein the step of producing the pattern of apertures includes determining position, size, length, number, and orientation of apertures in the pattern of apertures to be cut in the foam material to produce the desired set of cushioning characteristics.

* * * * *